US008296075B2

(12) United States Patent
Den Hartog

(10) Patent No.: US 8,296,075 B2
(45) Date of Patent: Oct. 23, 2012

(54) COMPUTER SYSTEM AND COMPUTER-FACILITATED METHOD FOR NUCLEIC ACID SEQUENCE ALIGNMENT AND ANALYSIS

(75) Inventor: Bobi Den Hartog, Santa Fe, NM (US)

(73) Assignee: Mito Tech, LLC, Santa Fe, NM (US)

( * ) Notice: Subject to any disclaimer, the term of this patent is extended or adjusted under 35 U.S.C. 154(b) by 267 days.

(21) Appl. No.: 12/469,035

(22) Filed: May 20, 2009

(65) Prior Publication Data

US 2009/0292665 A1 Nov. 26, 2009

Related U.S. Application Data

(60) Provisional application No. 61/054,981, filed on May 21, 2008.

(51) Int. Cl.
*G06F 19/00* (2011.01)
*G06F 15/00* (2006.01)
*G06F 17/30* (2006.01)
(52) U.S. Cl. .............................. 702/20; 700/1; 707/706
(58) Field of Classification Search .................. None
See application file for complete search history.

(56) References Cited

U.S. PATENT DOCUMENTS

2004/0142347 A1 7/2004 Stockwell et al.

FOREIGN PATENT DOCUMENTS

WO WO9966070 A1 12/1999

OTHER PUBLICATIONS

Monson et al. The mtDNA Population Database: An Integrated Software and Database Resource for Forensic Comparison Forensic Science Communications, vol. 4, No. 2 (2002).*
PCT International Search Report and Written Opinion in counterpart International Application No. PCT/US09/44626, (10 pages).
Anderson, S. et al. (1981) "Sequence and Organization of the Human Mitochondrial Genome," Nature 290:457-465.
Andrews R.M. et al. (1999) "Reanalysis and Revision of the Cambridge Reference Sequence for Human Mitochondrial DNA," Nature Genetics 23:147.
Bodenteich et al. (1991) "A Lifetime of Retinal Light Exposure Does Not Appear to Increase Mitochondrial Mutations," Gene 108(2):305-310.
Budowle, B. et al. (1999) "Mitochondrial DNA Regions HVI and HVII Population Data," Forensic Sci. Intl. 103:23-35.
Budowle, B. et al. (2003) "Forensics andMitochondrial DNA:Applications, Debates, and Foundations," Annu. Rev. Genomics Hum. Genet. 4:119-141.
Mike Coble presentation at the National Forensic Science Technology Center Mitochondrial DNA Workshop (Largo, FL), Mar. 13, 2006, "Introduction to Mitochondrial DNA Analysis"(pp. 1-24).
Kim, P.G. et al. (2008) "A Scaffold Analysis Tool Using Mate-Pair Information in Genome Sequencing," J. Biomed. Biotechnol. Article ID:675741 (7 pages).
Miller, K.W. et al. (2001) "A Compendium of Human Mitochondrial DNA Control Region: Development of an International Standard Forensic Database," Croatian Med. J. 42(3):315-327.
Montoya, J. et al. (1981) "Distinctive Features of the 5'-Terminal Sequences of the Human Mitochondrial mRNAs," Nature 290(9):465-470.
Sanchez-Villeda, H. et al. (2008) "DNAAlignEditor: DNA Alignment Editor Tool," BMC Bioinformatics 9:154-158.
Smith et al., "Identification of Common Molecular Subsequences", 1981, Journal of Molecular Biology 147: 195-197.
Smith, A.D. et al. (2008) "Using Quality Scores and Longer Reads Improves Accuracy of Solexa Read Mapping," BMC Bioinformatics 9:128-135.
Stoneking, M. (2000) "Hypervariable Sites in the mtDNA Control Region Are Mutational Hotspots," Am. J. Hum. Genet. 67:1029-1032.
Wilson et al., "Further Discussions of the Consistent Treatment of Length Variants in the Human Mitochondrial DNA Control Region", 2002, Forensic Sci. Comm., 4:4.
Wilson et al., "Recommendations for Consistent Treatment of Length Variants in the Human Mitochondrial DNA Control Region", Forensic Sci. Int., 2002, 129:35-42.
Yao et al., "A Call for mtDNA Data Quality Control in Forensic Science", 2004, Forensic Sci Int., 141(1):1-6.

* cited by examiner

*Primary Examiner* — John S Brusca
(74) *Attorney, Agent, or Firm* — Edell, Shapiro & Finnan, LLC

(57) ABSTRACT

The present invention relates to a computer system and methods of computer-facilitated data analysis for providing reliable DNA alignments. More specifically, the invention relates to the automation of alignment and naming of mitochondrial DNA sequences for use in forensic analysis. The methods of the present invention provide consistency of sequence nomenclature by minimizing alignment ambiguities, thus providing a common functional system within and among laboratories.

20 Claims, 2 Drawing Sheets

COMPUTER SYSTEM AND COMPUTER-FACILITATED METHOD FOR NUCLEIC ACID SEQUENCE ALIGNMENT AND ANALYSIS

CROSS-REFERENCE TO RELATED APPLICATIONS

This application claims priority to U.S. Patent Application Ser. No. 61/054,981 (filed May 21, 2008; pending), which application is herein incorporated by reference in its entirety.

STATEMENT REGARDING FEDERALLY-SPONSORED RESEARCH

This invention was made with government support under Contract Number J-FBI-05-170 awarded by the Federal Bureau of Investigation. The government has certain rights in the invention.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

1. Field of the Invention

The present invention relates to a computer system and method of computer-facilitated data analysis for providing reliable DNA alignments. More specifically, the invention relates to the automation of alignment and naming of mitochondrial DNA sequences, particularly for use in forensic analysis.

2. Description of Related Art

The process of DNA sequencing encompasses the use of biochemical methods for determining the order of the nucleotide bases: adenine, guanine, cytosine, and thymine, in a DNA oligonucleotide. The advent of rapid and efficient DNA sequencing techniques has significantly accelerated biological research and discovery. (Maxam et al., "A New Method For Sequencing DNA", 1977, Proc. Natl. Acad. Sci. (USA), 74(2):560-4; Braslavsky et al., "Sequence Information Can Be Obtained From Single DNA Molecules", 2003, Proc. Natl. Acad Sci. (USA) 100: 3960-3964; Ventner, J. C.; et al., "The Sequence Of The Human Genome", 2001, Science 291 (5507): 1304-51.) The rapid speed of sequencing attainable with modern DNA sequencing technology has been instrumental in the large-scale sequencing of the human genome, in the Human Genome Project. Related projects have generated the complete DNA sequences of many animal, plant, and microbial genomes (Blattner et al., "The Complete Genome Sequence of Escherichia coli K-12", 1997, Science 277 (5331): 1453-1462; The C. elegans Sequencing Consortium, "Genome Sequence of the Nematode C. elegans: A Platform for Investigating Biology", 1998, Science 282 (5396): 2012-2018; Neil Hall, "Advanced Sequencing Technologies And Their Wider Impact In Microbiology", 2007, The Journal of Experimental Biology 209: 1518-1525).

The sequence of a DNA molecule constitutes the heritable genetic information in nuclei, plasmids, mitochondria, and chloroplasts that forms the basis for the developmental programs of all living organisms. Determining the DNA sequence is therefore useful in basic research studying fundamental biological processes, as well as in applied fields such as diagnostic research or forensic analysis. Single nucleotide polymorphisms (SNPs) are an abundant form of nucleic acid sequence variation, occurring at a rate of approximately one per 500 nucleotides in coding sequences, and more abundantly in non-coding sequence (U.S. Pat. No. 7,273,699; Wang D. G., et al. (1998) Science 280:1077-1082). As many as a million SNPs may exist in the human genome. The accurate identification and characterization of single nucleotide polymorphisms (SNPs) has important utility in genome-wide association studies and genetic linkage studies (U.S. Pat. No. 7,361,468) as well as in personalized therapeutic and diagnostic protocols (U.S. Pat. Nos. 7,488,813; 7,127,355; 7,488,813; 7,470,513; 7,461,048; 7,461,006; 6,931,326).

In bioinformatics, a sequence alignment is a way of arranging two or more primary sequences of DNA, RNA, or proteins to identify regions of similarity between a "query" or "sample" sequence and a "reference" sequence that may be a consequence of functional, structural, or evolutionary relationships between the sequences. Alignments are commonly represented both graphically and in text format. In almost all sequence alignment representations, sequences are written in rows arranged so that aligned residues appear in successive columns. In text formats, aligned columns containing identical or similar characters are indicated with a system of conservation symbols. An asterisk is often used to show identity between two columns; other less common symbols include a colon for conservative substitutions and a period for semiconservative substitutions. Many sequence visualization programs also use color to display information about the properties of the individual sequence elements; in DNA and RNA sequences, this involves assigning each nucleotide its own color. For multiple sequences the last row in each column is often the consensus sequence determined by the alignment; the consensus sequence is also often represented in graphical format with a sequence logo in which the size of each nucleotide or amino acid letter corresponds to its degree of conservation (Schneider et al., "Sequence Logos: A New Way To Display Consensus Sequences", 1990, Nucleic Acids Res. 18: 6097-6100).

Such pairwise alignments of reference and query/sample sequences may be performed globally, locally or in a hybrid ("glocal") fashion. (Needleman et al., "A General Method Applicable To The Search For Similarities In The Amino Acid Sequence Of Two Proteins", 1970, J Mol Biol. 48(3):443-53; Smith et al., "Identification Of Common Molecular Subsequences", 1981, Journal of Molecular Biology 147: 195-197; Brudno et al., "Glocal Alignment: Finding Rearrangements During Alignment", 2003, Bioinformatics 19 Suppl 1: i54-62). Global alignments, which attempt to align every residue of the reference sequence with every residue of the query/sample sequences, are most useful when the sequences in the query/sample set are similar and are of approximately equal size to the reference sequence. A general global alignment technique is called the Needleman-Wunsch algorithm and is based on dynamic programming (Phillips, A. J., "Homology Assessment And Molecular Sequence Alignment," 2006, J. Biomed. Inform. 39(1):18-33). Local alignments have particular utility for dissimilar sequences that are suspected to contain regions of similarity or similar sequence motifs within their larger sequence context. The Smith-Waterman algorithm, a general local alignment method also based on dynamic programming, is often employed (Bucher, P. et al., "A Sequence Similarity Search Algorithm Based On A Probabilistic Interpretation Of An Alignment Scoring System," 1996, Proc. Int. Conf. Intell. Syst. Mol. Biol. 4:44-51).

Instead of looking at the total sequence, the Smith-Waterman algorithm compares segments of all possible lengths and optimizes the similarity measure. Hybrid methods, known as semiglobal or "glocal" methods, attempt to find the best possible alignment that includes the start and end of one or the other sequence.

One application of the currently available DNA sequencing and alignment technologies is in the area of genetic fingerprinting. Genetic fingerprinting is a technique used to distinguish between individuals of the same species using only samples of their DNA. Although two individuals of the same species will have the vast majority of their DNA sequence in common, certain sequences, known as highly variable repeat sequences called variable number tandem repeat loci (VNTRs) will vary within a population. These loci are variable enough that two unrelated humans are unlikely to have the same alleles. (Jeffreys et al., "*Hypervariable 'Minisatellite' Regions In Human DNA*", 1985, Nature 314: 67-73) The technique is now the basis of several national DNA identification databases. These databases serve as an invaluable resource for researchers, investigators, and forensic scientists. Genetic fingerprinting has been widely applied to provide detailed genetic information for researchers in fields as varied as population genetics, microbiology and legal ethics (McClelland et al., "*A Genetic Linkage Map For Coho Salmon (Oncorhynchus kisutch)*", 2008, Anim Genet., 39(2): 169-79; Minder et al., "*A Population Genomic Analysis Of Species Boundaries: Neutral Processes, Adaptive Divergence And Introgression Between Two Hybridizing Plant Species*", 2008, Mol Ecol., 17(6):1552-63; Daeid, N., "*DNA-What's Next?*", 2007, Sci. Justice, 47(4): 149; Stellaroli et al., "*Shared Genetic Data And The Rights Of Involved People*", 2007, Law Hum Genome Rev. (26):193-231; Kronforst et al., "*The Population Genetics Of Mimetic Diversity In Heliconius Butterflies*", 2008, Proc Biol Sci., 275(1634):493-500).

Methods used for DNA fingerprinting include restriction fragment length polymorphism typing of variable number tandem repeat (VNTR) loci (Budowle et al., "*Modifications To Improve The Effectiveness Of Restriction Fragment Length Polymorphism Typing*", Appl. Theor. Electrophoresis, 1990, 1: 181-187; Jeffreys et al., "*Hypervariable Minisatellite Regions In Human DNA*", Nature, 1985, 314:67-73; Jeffreys et al., "*Individual-Specific Fingerprints Of Human DNA*", Nature, 1985, 316:76-79; Wyman et al., "*A Highly Polymorphic Locus In Human DNA*", Proc. Natl. Acad. Sci. (USA), 1980, 77:6754-6758), polymerase chain reaction (PCR)-based systems to analyze single nucleotide polymorphisms (SNPs) (Comey et al., "*Validation Studies On The Analysis Of The Hla-Dq Alpha Locus Using The Polymerase Chain Reaction*", J. Forensic Sci., 1991, 36: 1633-1648; Saiki et al., "*Genetic Analysis Of Amplified DNA With Immobilized Sequence-Specific Oligonucleotide Probes*", Proc. Natl. Acad. Sci. (USA), 1989, 86: 6230-6234), VNTR loci (Budowle et al., "*Analysis Of The VNTR Locus D1S80 By The PCR Followed By High-Resolution PAGE*", Am. J. Hum. Genet., 1991, 48:137-144; Kasai et al., "*Amplification Of A Variable Number Of Tandem Repeat (VNTR) Locus (pMCT118) By The Polymerase Chain Reaction (PCR) And Its Application To Forensic Science*", J. Forensic Sci., 1990, 35:1196-1200), short tandem repeat loci (STR) (Edwards et al., "*DNA Typing And Genetic Mapping With Trimeric And Tetrameric Tandem Repeats*", Am. J. Hum. Genet., 1991, 49:746-756), Y chromosome analysis (Koyama et al., "*Utility Of Y-STR Haplotype And mtDNA Sequence In Personal Identification Of Human Remains*", 2002, Am J Forensic Med Pathol. 23(2):181-185) and mitochondrial DNA analysis (Holland et al., "*Mitochondrial DNA Analysis Of Human Skeletal Remains: Identification Of Remains From The Vietnam War*", J. Forensic Sci., 1993, 38:542-553; Hopgood et al., "*Strategies For Automated Sequencing Of Human Mitochondrial DNA Directly From PCR Products*", Biotechniques, 1992, 13:82-92; Sullivan et al., "*Automated Amplification And Sequencing Of Human Mitochondrial DNA*", Electrophoresis, 1991, 12:17-21; Wilson et al., "*Validation Of Mitochondrial DNA Sequencing For Forensic Casework Analysis*", Int. J. Leg. Med., 1995, 108:68-74; Wilson et al., "*Extraction, PCR Amplification, And Sequencing Of Mitochondrial DNA From Human Hair Shafts*", Biotechniques, 1995, 18:662-669).

Particularly for forensic scientists, DNA fingerprinting based on sequence analysis is an important tool for identifying genetic material of unknown origin (Pretty, I., "*Forensic Dentistry: 1. Identification Of Human Remains*", 2007, Dent Update, 34(10):621-2, 624-6, 629-30; Baker et al., "*Reuniting Families: An Online Database To Aid In The Identification Of Undocumented Immigrant Remains*", 2008, J Forensic Sci., 53(1):50-3; Irwin et al., "*Application Of Low Copy Number STR Typing To The Identification Of Aged, Degraded Skeletal Remains*", 2007, J Forensic Sci., 52(6):1322-7; LeClair et al., "*Bioinformatics And Human Identification In Mass Fatality Incidents: The World Trade Center Disaster*", 2007, J Forensic Sci. 52(4):806-19). Common sources of genetic material may include, but are not limited to, skin, hair, saliva, tissue, bone, and blood. Preservation of sequence integrity is vital to assure proper sequence identification; however, this is not always possible, and often samples are contaminated or partially degraded.

Mitochondria are DNA-containing organelles that supply energy to cells and contain their own DNA. Mitochondrial DNA (mtDNA) is a particularly preferred source of DNA for sequence analysis due to its high copy number and resistance to degradation (Remualdo et al., "*Analysis Of Mitochondrial DNA From The Teeth Of A Cadaver Maintained In Formaldehyde*", 2007, Am J Forensic Med Pathol., 28(2):145-6; Andreasson et al., "*Nuclear And Mitochondrial DNA Quantification Of Various Forensic Materials*", 2006, Forensic Sci Int., 164(1):56-64; Matsuda et al., "*Identification Of DNA Of Human Origin Based On Amplification Of Human-Specific Mitochondrial Cytochrome b Region*", 2005, Forensic Sci Int. Sep. 10, 2005; 152(2-3):109-14).

Human mtDNA contains approximately 16,500 base pairs, of which there are two regions that contain significant sequence variation and can provide distinguishing profiles useful in identifying individuals or genetic samples. Sample identifications are based on the observation that mtDNA from an individual and from that individual's maternal relatives have the same sequences present in the two regions of mtDNA sequence conservation (Case et al., "*Maternal Inheritance Of Mitochondrial DNA Polymorphisms In Cultured Human Fibroblasts*", Somat. Cell Genet., 1981, 7:103-108; Giles et al., "*Maternal Inheritance Of Human Mitochondrial DNA*", Proc. Natl. Acad. Sci. (USA), 1980, 77:6715-6719). In contrast, non-related individuals will have different sequences in these two regions of mtDNA. Forensic analysis using mtDNA is thus performed by comparing an individual's mtDNA with mtDNA isolated from an individual suspected of being a maternal relative. By obtaining genetic material from a candidate maternal relative, an investigator may compare the mtDNA sequences for purposes of sample identification. If the sample mtDNA does not match that of the presumed maternal relative in more than two positions, then a familial connection may be excluded (Bender et al., "*Application Of MtDNA Sequence Analysis In Forensic Casework For The Identification Of Human Remains*", 2000, Forensic Sci Int., 113(1-3):103-7; Szibor et al., "*Efficiency Of Forensic mtDNA Analysis. Case Examples Demonstrating The Identification Of Traces*", 2000, Forensic Sci Int., 113(1-3):71-8).

Despite the many advances in DNA sequencing and alignment technology, current methods for performing forensic DNA analysis are labor-intensive, and often result in the same sequence typed differently by different investigators due to the necessity for human evaluation of the sequencing data. Further compounding this issue is the database contamination resulting from human error in sequence evaluation (Carracedo et at., "*Reproducibility Of mtDNA Analysis Between Laboratories: A Report Of The European DNA Profiling Group (EDNAP)*", 1998, Forensic Sci Int., 97(2-3):165-70; Yao et at., "*A Call For mtDNA Data Quality Control In Forensic Science*", 2004, Forensic Sci Int., 141(1):1-6; Budowle et al., "*Addressing The Use Of Phylogenetics For Identification Of Sequences In Error In The SWGDAM Mitochondrial DNA Database*", 2004, J Forensic Sci., 49(6):1256-61).

In particular, the manner in which sequence alignments are described can vary from laboratory to laboratory, thereby creating ambiguities in future analyses. To address this problem, Wilson et al. (Wilson et al., "*Recommendations For Consistent Treatment Of Length Variants In The Human Mitochondrial DNA Control Region*", Forensic Sci. Int., 2002, 129:35-42; Wilson et al., "*Further Discussions Of The Consistent Treatment Of Length Variants In The Human Mitochondrial DNA Control Region*", 2002, Forensic Sci. Comm., 4:4) developed an approach to standardize alignments using differential weighting of transitions, transversions, insertions and deletions. The Wilson method provided recommendations for forensic scientists to assist them in interpreting and naming the mtDNA sequence data generated. By utilizing this method, inconsistencies in nomenclature could be reduced, and from the higher quality databases generated by the use of this method, more reliable profile searches could be performed.

Although the goal of these rules was to standardize sequence nomenclature in order to provide greater consistency in forensic DNA data, several issues have become apparent. First, the Wilson Rules are currently performed manually, and are extremely time-consuming to implement, resulting in fewer samples being analyzed by forensic scientists, and thus, fewer entries into reference databases. Additionally, the rules as written do not guarantee consistent identification with the traditional nomenclature due to the necessity for human interpretation of sequence data. Therefore, a need exists for a computer-facilitated method of aligning mtDNA sample sequences with reference samples that allows for rapid sequence alignment, provides for absolute stability and consistency of nomenclature and provides increased database accuracy. The present invention is directed to this and other goals.

SUMMARY OF THE INVENTION

The present invention relates to a computer system and method of computer-facilitated data analysis for providing reliable DNA alignments. More specifically, the invention relates to the automation of alignment and naming of mitochondrial DNA sequences, particularly for use in forensic analysis. The methods of the present invention provide consistency of sequence nomenclature by minimizing alignment ambiguities, thus providing a common functional system within and among laboratories.

In detail, the invention provides a method for optimally aligning a first polynucleotide sequence (I) to a second polynucleotide sequence (II) to provide a determination of their similarity, wherein the method employs a device that is programmed to perform the steps of:
 (A) receiving the sequences (I) and (II) into memory and processing the received sequences to generate a set of possible alignments between the sequences;
 (B) applying a hierarchical alignment rule to the generated alignments and selecting alignment(s) that comply with the applied alignment rule; wherein the alignment rule is a member of a hierarchical set of alignment rules composed of an initial rule and one or more hierarchically ordered additional rule(s);
 (C) (1) where the application of the applied alignment rule results in only a single compliant alignment, reporting the alignment as the optimal alignment; or
  (2) where the application of the applied alignment rule does not result in only a single compliant alignment, applying the next additional hierarchical alignment rule to the alignments and selecting alignment(s) that comply with the applied next additional hierarchical alignment rule; and
 (D) repeating the step (C) until the application of an applied alignment rule results in only a single compliant alignment, and reporting the alignment as the optimal alignment.

The invention further concerns the embodiments of such method wherein at least one of the sequences (I) and (II) is a sample sequence; wherein at least one of the sequences (I) and (II) is a reference sequence or wherein at least one of the sequences (I) and (II) is a query sequence. The invention further concerns the embodiments of such methods wherein (I) and (II) are DNA (especially wherein the DNA is mtDNA). The invention further concerns the embodiments of such methods wherein the sequences (I) and (II) are HV2CS mtDNA sequences.

The invention further concerns the embodiments of such methods wherein, in step (A), the set of possible alignments contains a subset of the set of every possible alignment between sequences (I) and (II). The invention further concerns the embodiments of such methods wherein, in step (A), the set of possible alignments contains every possible alignment between sequences (I) and (II).

The invention further concerns the embodiments of such methods wherein the hierarchical set of alignment rules comprises:
the initial alignment rule:
 (1) selecting from the alignments of the step (A) the possible alignments with the lowest number of differences between sequence (I) and sequence (II) and eliminating all other generated possible alignments generated in the step (A) from further processing;
and at least one additional hierarchically ordered alignment rule selected from the group consisting of:
 (2) selecting from any alignments remaining after application of the initial rule (1) those alignments in which the AC motif of the polynucleotide sequence: ACACACA-CACC (SEQ ID NO:1) is maximally preserved and any insertions or deletions are located 3' to the AC motif, and eliminating all other generated possible alignments from further processing;
 (3) selecting from any alignments remaining after application of a previously applied alignment rule (1) or (2) those alignments containing substitutions rather than insertions or deletions, and eliminating all other generated possible alignments from further processing;

(4) selecting from any alignments remaining after application of a previously applied alignment rule (1), (2) or (3) those alignments containing transitions rather than transversions, and eliminating all other generated possible alignments from further processing;

(5) selecting from any alignments remaining after application of a previously applied alignment rule (1), (2), (3) or (4) those alignments in which insertions or deletions are placed contiguously, and eliminating all other generated possible alignments from further processing;

(6) selecting from any alignments remaining after application of a previously applied alignment rule (1), (2), (3), (4) or (5) those alignments which place insertions or deletions 3' to a homopolymeric stretch present in the sequences (I) and (II), and eliminating all other generated possible alignments from further processing; and (7) selecting from any alignments remaining after application of a previously applied alignment rule (1), (2), (3), (4), (5) or (6) those alignments in which insertions or deletions are placed 3'-most, and eliminating all other generated possible alignments from further processing.

The invention further concerns the embodiment of such above-described method wherein the applied hierarchical rules comprise the initial rule and in hierarchical order one, two, three, four, five, or six of the additional hierarchically ordered rules. The invention particularly concerns the embodiment of such methods wherein the applied hierarchical rules comprise all of the rules (1), (2), (3), (4), (5), (6) and (7).

The invention further concerns the embodiments of such methods wherein the sequences (I) and (II) are HV2CS mtDNA sequences, and wherein the hierarchical set of alignment rules comprises:

the initial alignment rule:
(1) selecting from the alignments of the step (A) the possible alignments in which the polynucleotide sequence: AAACCCCCCC TCCCCC SEQ ID NO:2 is maximally preserved, and eliminating all other generated possible alignments generated in the step (A) from further processing;

and at least one additional hierarchically ordered alignment rule selected from the group consisting of:

2) selecting from alignments remaining after application of the initial alignment rule (1) the possible alignments with the lowest number of differences between sequence (I) and sequence (II) and eliminating all other generated possible alignments from further processing;

(3) selecting from any alignments remaining after application of a previously applied alignment rule (1) or (2) those alignments containing substitutions rather than insertions or deletions, and eliminating all other generated possible alignments from further processing;

(4) selecting from any alignments remaining after application of a previously applied alignment rule (1), (2) or (3) those alignments containing transitions rather than transversions, and eliminating all other generated possible alignments from further processing;

(5) selecting from any alignments remaining after application of a previously applied alignment rule (1), (2), (3) or (4) those alignments which place insertions or deletions 3' to any homopolymeric stretches present in the sequences (I) and (II), and eliminating all other generated possible alignments from further processing;

(6) selecting from any alignments remaining after application of a previously applied alignment rule (1), (2), (3), (4) or (5) those alignments in which insertions or deletions are placed contiguously, and eliminating all other generated possible alignments from further processing;

(7) selecting from any alignments remaining after application of a previously applied alignment rule (1), (2), (3), (4), (5) or (6) those alignments in which insertions or deletions are placed 3'-most, and eliminating all other generated possible alignments from further processing.

The invention further concerns the embodiment of such above-described method wherein the applied hierarchical rules comprise the initial rule and in hierarchical order one, two, three, four, five, or six of the additional hierarchically ordered rules. The invention particularly concerns the embodiment of such methods wherein the applied hierarchical rules comprise all of the rules (1), (2), (3), (4), (5), (6) and (7).

The invention also provides a computer system comprising:

memory for storing alignment algorithm computer programming instructions and sequence data and for storing the results of the implementation of the alignment algorithm, a processor for accessing and implementing the rules of the algorithm;

input means; and means for imparting the results of the analysis to users of the computer system, wherein the alignment algorithm computer programming instructions comprise instructions for causing the computer system to optimally align a first polynucleotide sequence (I) to a second polynucleotide sequence (II) to provide a determination of their similarity by performing the steps of:

(A) receiving the sequences (I) and (II) into memory and processing the received sequences to generate a set of possible alignments between the sequences;

(B) applying a hierarchical alignment rule to the generated alignments and selecting alignment(s) that comply with the applied alignment rule; wherein the alignment rule is a member of a hierarchical set of alignment rules composed of an initial rule and one or more hierarchically ordered additional rule(s);

(C) (1) where the application of the applied alignment rule results in only a single compliant alignment, reporting the alignment as the optimal alignment; or
(2) where the application of the applied alignment rule does not result in only a single compliant alignment, applying the next additional hierarchical alignment rule to the alignments and selecting alignment(s) that comply with the applied next additional hierarchical alignment rule; and (D) repeating the step (C) until the application of an applied alignment rule results in only a single compliant alignment, and reporting the alignment as the optimal alignment.

The invention further concerns the embodiments of such computer system wherein at least one of the sequences (I) and (II) is a sample sequence; wherein at least one of the sequences (I) and (II) is a reference sequence or wherein at least one of the sequences (I) and (II) is a query sequence. The invention further concerns the embodiments of such methods wherein (I) and (II) are DNA (especially wherein the DNA is mtDNA). The invention further concerns the embodiments of such methods wherein the sequences (I) and (II) are HV2CS mtDNA sequences.

The invention further concerns the embodiments of such methods wherein, in step (A), the set of possible alignments contains a subset of the set of every possible alignment between sequences (I) and (II). The invention further concerns the embodiments of such methods wherein, in step (A), the set of possible alignments contains every possible alignment between sequences (I) and (II).

The invention further concerns the embodiments of such computer systems wherein the hierarchical set of alignment rules comprises:

the initial alignment rule:
(1) selecting from the alignments of the step (A) the possible alignments with the lowest number of differences between sequence (I) and sequence (II) and eliminating all other generated possible alignments generated in the step (A) from further processing;

and at least one additional hierarchically ordered alignment rule selected from the group consisting of:
(2) selecting from any alignments remaining after application of the initial rule (1) those alignments in which the AC motif of the polynucleotide sequence: ACACACACACC (SEQ ID NO:1) is maximally preserved and any insertions or deletions are located 3' to the AC motif, and eliminating all other generated possible alignments from further processing;
(3) selecting from any alignments remaining after application of a previously applied alignment rule (1) or (2) those alignments containing substitutions rather than insertions or deletions, and eliminating all other generated possible alignments from further processing;
(4) selecting from any alignments remaining after application of a previously applied alignment rule (1), (2) or (3) those alignments containing transitions rather than transversions, and eliminating all other generated possible alignments from further processing;
(5) selecting from any alignments remaining after application of a previously applied alignment rule (1), (2), (3) or (4) those alignments in which insertions or deletions are placed contiguously, and eliminating all other generated possible alignments from further processing;
(6) selecting from any alignments remaining after application of a previously applied alignment rule (1), (2), (3), (4) or (5) those alignments which place insertions or deletions 3' to a homopolymeric stretch present in the sequences (I) and (II), and eliminating all other generated possible alignments from further processing; and
(7) selecting from any alignments remaining after application of a previously applied alignment rule (1), (2), (3), (4), (5) or (6) those alignments in which insertions or deletions are placed 3'-most, and eliminating all other generated possible alignments from further processing.

The invention further concerns the embodiment of such above-described computer system wherein the applied hierarchical rules comprise the initial rule and in hierarchical order one, two, three, four, five, or six of the additional hierarchically ordered rules. The invention particularly concerns the embodiment of such methods wherein the applied hierarchical rules comprise all of the rules (1), (2), (3), (4), (5), (6) and (7).

The invention further concerns the embodiments of such computer systems wherein the sequences (I) and (II) are HV2CS mtDNA sequences, wherein the hierarchical set of alignment rules comprises:

the initial alignment rule:
(1) selecting from the alignments of the step (A) the possible alignments in which the polynucleotide sequence: AAACCCCCCC TCCCCC SEQ ID NO:2 is maximally preserved, and eliminating all other generated possible alignments generated in the step (A) from further processing;

and at least one hierarchically ordered alignment rule selected from the group consisting of:
(2) selecting from alignments remaining after application of the initial alignment rule (1) the possible alignments with the lowest number of differences between sequence (I) and sequence (II) and eliminating all other generated possible alignments from further processing;
(3) selecting from any alignments remaining after application of a previously applied alignment rule (1) or (2) those alignments containing substitutions rather than insertions or deletions, and eliminating all other generated possible alignments from further processing;
(4) selecting from any alignments remaining after application of a previously applied alignment rule (1), (2) or (3) those alignments containing transitions rather than transversions, and eliminating all other generated possible alignments from further processing;
(5) selecting from any alignments remaining after application of a previously applied alignment rule (1), (2), (3) or (4) those alignments which place insertions or deletions 3' to any homopolymeric stretches present in the sequences (I) and (II), and eliminating all other generated possible alignments from further processing;
(6) selecting from any alignments remaining after application of a previously applied alignment rule (1), (2), (3), (4) or (5) those alignments in which insertions or deletions are placed contiguously, and eliminating all other generated possible alignments from further processing;
(7) selecting from any alignments remaining after application of a previously applied alignment rule (1), (2), (3), (4), (5) or (6) those alignments in which insertions or deletions are placed 3'-most, and eliminating all other generated possible alignments from further processing.

The invention further concerns the embodiment of such above-described computer system wherein the applied hierarchical rules comprise the initial rule and in hierarchical order one, two, three, four, five, or six of the additional hierarchically ordered rules. The invention particularly concerns the embodiment of such methods wherein the applied hierarchical rules comprise all of the rules (1), (2), (3), (4), (5), (6) and (7).

DETAILED DESCRIPTION OF THE INVENTION

Figure 1:
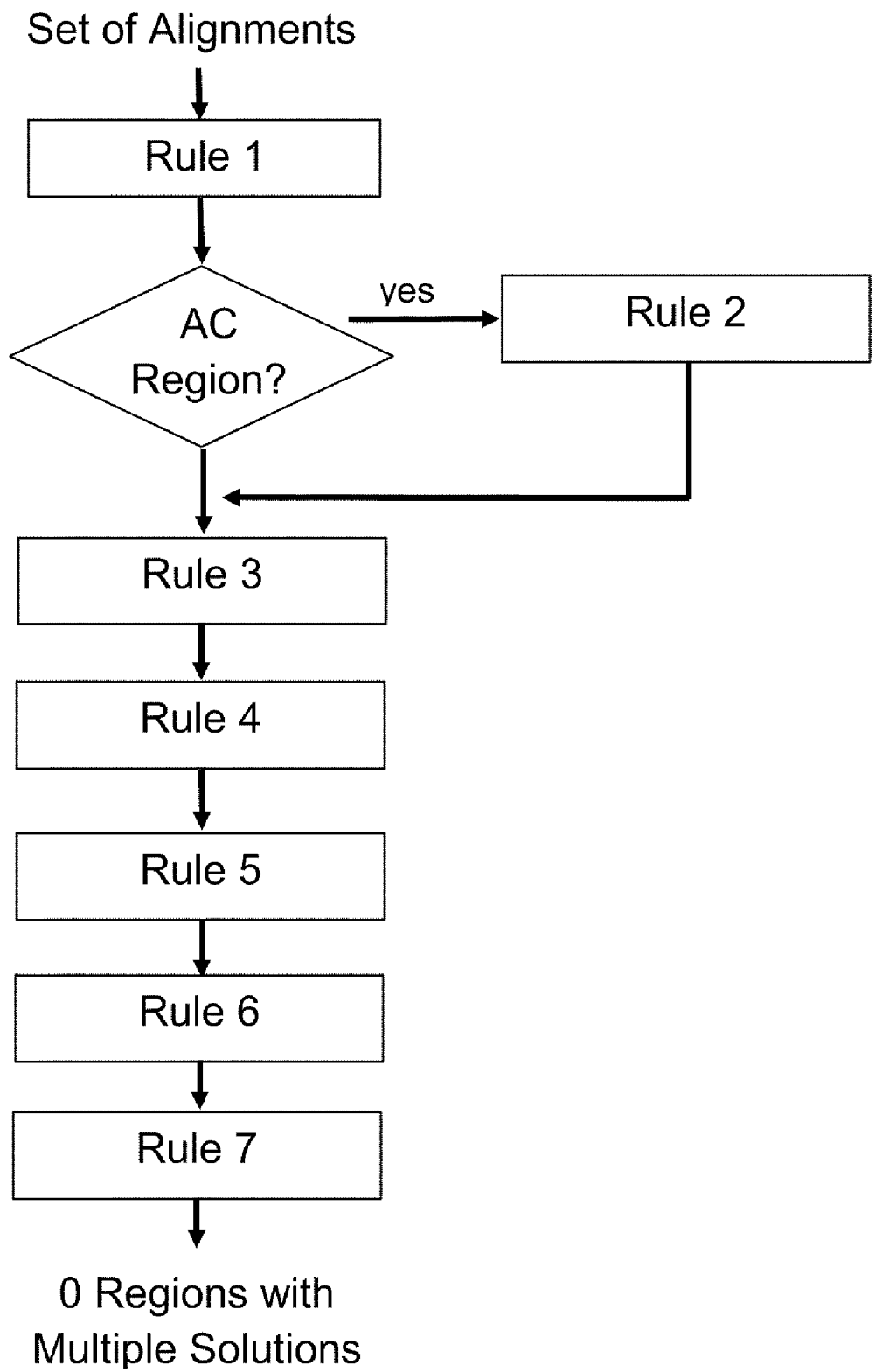
FIG. 1 shows a block diagram of the hierarchical method used by the system and methods of the present invention for sorting possible alignment sequences.

The present invention relates to a computer system and method of computer-facilitated data analysis for providing reliable DNA alignments. More specifically, the invention relates to the automation of alignment and naming of mitochondrial DNA sequences for use in forensic analysis. The methods of the present invention provide consistency of sequence nomenclature by minimizing alignment ambiguities, thus providing a common functional system within and among laboratories.

In various embodiments, the present invention discloses a system and methods for analyzing DNA sequence data and information of reference, sample and query sequences. As used herein, the term "reference" sequence denotes sequence information of known origin or identity. The term "sample" sequence denotes sequence information obtained from a sample obtained from any source of nucleic acid; for example, blood, hair, cells, semen, saliva, tears, purified DNA, etc. The term "query" sequence is used to refer to sequence information identified in accordance with the invention that shares identity or homology with a reference sequence or a sample sequence. The reference, sample or query sequence information is preferably from mitochondrial DNA or nuclear DNA. Such sequence information may be obtained from computer-facilitated sequencers, or any other technology or methodology for obtaining DNA sequences known in the art. Thus, in one embodiment, DNA is obtained from a sample ("sample" sequence) and compared to DNA of a known individual or known reference (both considered "reference" sequences). In an alternative embodiment, DNA is obtained from a sample ("sample" sequence) and compared to sequence information in, for example, a database of sequence information to identify individuals having DNA ("query" sequences) that shares identity or homology to such sample sequence.

The present invention accomplishes such goals through the use of process rules for optimally aligning a sample sequence to a reference sequence or a query sequence. As used herein, the term "optimally aligning" is intended to denote one or more alignments that best complies/comply with the alignment rules of the present invention. Such optimal aligning may identify more than one alignment because two or more alignments may each comply equally well and may each comply better than all other considered alignments (i.e., each such alignment may comprise an alignment in which a rule criterion has been "maximally preserved").

In other embodiments, the present invention describes a computer-facilitated sequence analysis system and methods for use by said system to provide reliable mtDNA profiles useful for comparison of forensic samples with reference samples. Additionally, certain embodiments provide a computer-facilitated system and methods for naming mtDNA sequences according to standardized nomenclature and accepted standards within the forensics community.

In some embodiments, the computer-facilitated system and methods of the present invention include incorporating data analysis rules or procedures derived from manual review techniques associated with analysis of mtDNA samples. Examples of data analysis rules include, but are not limited to, rules regarding preferences for insertion/deletion placement, motif placement, number and location of differences from reference sequences, etc. Preferred embodiments of the invention incorporate a hierarchical method for said data analysis, in which a set of possible alignments for a given set of sequences are generated, and through application of the one or more hierarchically ordered rules, an optimal alignment sequence is generated. As used herein, the term "hierarchically ordered" denotes that rules are applied in ordinal order, so that for any two applied rules, the rule having the lower ordinal number is applied first (for example, if rules (1), (2), (5) and (7) are to be applied, they would be applied in the sequential order: (1), (2), (5) and then (7)).

In still another embodiment, the present invention encompasses a computer-readable medium having stored thereon instructions which cause a general-purpose computer to perform the steps of: (a) acquiring sequence information from at least one sample and at least one reference sample; (b) generating a set of possible alignments between the sample and reference sequences; (c) evaluating the set of possible alignments by eliminating those alignments that do not conform to user-input parameters; and (d) providing a sequence alignment that best conforms to said user-input parameters.

In yet another embodiment, the present invention encompasses a computer-based system for performing computer-facilitated sequence analysis between a target sample of and at least one reference sample, the system comprising: (a) a database for storing sequence alignment information describing the composition and characteristics of a plurality of nucleotides relating to the mitochondrial DNA sequence of the target sample and at least one reference sample; (b) a program which performs the operations of: (i) generating a set of possible alignments between said target sequence and said at least one reference sequence; (ii) evaluating said set of possible alignments utilizing a hierarchical set of rules, resulting in the elimination of alignments that do not conform to the rules; wherein each hierarchical rule is applied only if multiple possible alignments remain after application of a preceding hierarchical rule; and (iii) repeating step (ii) until one alignment remains, wherein the remaining alignment is the desired optimal alignment.

While various embodiments of the present teachings are directed towards computer-facilitated analysis of sequence information described in the context of sample identification using mitochondrial DNA sequence data, one skilled in the art will recognize that the computer systems and methods described herein may similarly be configured to implement other types of sequencing applications, such as nuclear DNA sequence alignment or RNA sequence alignment.

Mitochondrial DNA (mtDNA) provides an extracellular genome that has certain features that make it desirable for use in forensics, namely, high copy number, lack of recombination, and matrilineal inheritance. mtDNA typing has become routine in forensic biology and is used to analyze bones, teeth, hair shafts, and other biological samples in which the nuclear DNA content may be too low to analyze. To evaluate results obtained by sequencing the two hypervariable regions of the control region of the human mtDNA genome, one must consider the genetically related issues of nomenclature, reference population databases, heteroplasmy, paternal leakage, recombination, and interpretation of results. DNA typing methods include restriction fragment length polymorphism typing of variable number tandem repeat (VNTR) loci (Budowle et al., "*Modifications To Improve The Effectiveness Of Restriction Fragment Length Polymorphism Typing*", Appl. Theor. Electrophoresis, 1990, 1: 181-187; Jeffreys et al., "*Hypervariable Minisatellite Regions In Human DNA*", Nature, 1985, 314:67-73; Jeffreys et al., "*Individual-Specific Fingerprints Of Human DNA*", Nature, 1985, 316:76-79; Wyman et al., "*A Highly Polymorphic Locus In Human DNA*", Proc. Natl. Acad. Sci. (USA), 1980, 77:6754-6758), polymerase chain reaction (PCR)-based systems to analyze single nucleotide polymorphisms (SNPs) (Comey et al., "*Validation Studies On The Analysis Of The Hla-Dq Alpha Locus Using The Polymerase Chain Reaction*", J. Forensic Sci., 1991, 36: 1633-1648; Saiki et al., "*Genetic Analysis Of Amplified DNA With Immobilized Sequence-Specific Oligonucleotide Probes*", Proc. Natl. Acad. Sci. (USA), 1989, 86: 6230-6234), VNTR loci (Budowle et al., "*Analysis Of The VNTR Locus D1S80 By The PCR Followed By High-Resolution PAGE*", Am. J. Hum. Genet., 1991, 48:137-144; Kasai et al., "*Amplification Of A Variable Number Of Tandem Repeat (VNTR) Locus (pMCT118) By The Polymerase Chain Reaction (PCR) And Its Application To Forensic Science*", J. Forensic Sci., 1990, 35:1196-1200), short tandem repeat loci (STR) (Edwards et al., "*DNA Typing And Genetic Mapping With Trimeric And Tetrameric Tandem Repeats*", Am. J. Hum. Genet., 1991, 49:746-756), and direct sequencing of mitochondrial DNA (Holland et al., "*Mitochondrial DNA Analysis Of Human Skeletal Remains: Identification Of Remains From The Vietnam War*", J. Forensic Sci., 1993, 38:542-553; Hopgood et al., "*Strategies For Automated Sequencing Of Human Mitochondrial DNA Directly From PCR Products*", Biotechniques, 1992, 13:82-92; Sullivan et al., "*Automated Amplification And Sequencing Of Human Mitochondrial DNA*", Electrophoresis, 1991, 12:17-21; Wilson et al., "*Validation Of Mitochondrial DNA Sequencing For Forensic Casework Analysis*", Int. J. Leg. Med., 1995, 108:68-74; Wilson et al., "*Extraction, PCR Amplification, And Sequencing Of Mitochondrial DNA From Human Hair Shafts*", Biotechniques, 1995, 18:662-669).

I. Mitochondrial DNA

The mitochondrial genome has been completely sequenced (Anderson et al., "*Sequence And Organization Of The Human Mitochondrial Genome*", Nature, 1981, 290:457-465). One strand of mtDNA (the "heavy strand") is purine-rich, and conversely, the complement strand (the "light strand") is pyrimidine-rich. Nucleotide positions in the mtDNA genome are numbered according to the convention of Anderson et al. (Anderson et al., "*Sequence And Organization Of The Human Mitochondrial Genome*", Nature, 1981, 290:457-465), as modified by (Andrews et al., "*Reanalysis And Revision Of The Cambridge Reference Sequence For Human Mitochondrial DNA*", Nature Genetics, 1999, 23:147). The mtDNA polymerase has a low fidelity, and there is no apparent mtDNA repair mechanism; therefore, there is a much higher mutation rate in mtDNA than in nuclear DNA. In fact, some regions of the mtDNA genome evolve at rates nearly 10 times that of a single-copy nuclear gene. These variable regions are of particular interest and value for human identity testing. Most of the sequence variation between individuals is found within two specific segments of the control region: hypervariable region 1 (HV1) and hypervariable region 2 (HV2) (Greenberg et al., "*Intraspecific Nucleotide Sequence Variability Surrounding The Origin Of Replication In Human Mitochondrial DNA*", Gene, 1983, 21:33-49). Typically, HV1 spans the region between nucleotides 16,024 and 16,365, and HV2 spans nucleotides 73 to 340. The small size of these two regions makes them particularly amenable to amplification by PCR; hence, HV1 and HV2 are routinely typed for forensic testing purposes.

The mitochondrial genome has been completely sequenced (Anderson et al., "*Sequence And Organization Of The Human Mitochondrial Genome*", Nature, 1981, 290:457-465). One strand of mtDNA (the "heavy strand") is purine-rich, and conversely, the complement strand (the "light strand") is pyrimidine-rich. Nucleotide positions in the mtDNA genome are numbered according to the convention of Anderson et al. (Anderson et al., "*Sequence And Organization Of The Human Mitochondrial Genome*", Nature, 1981, 290:457-465), as modified by (Andrews et al., "*Reanalysis And Revision Of The Cambridge Reference Sequence For Human Mitochondrial DNA*", Nature Genetics, 1999, 23:147). The mtDNA polymerase has a low fidelity, and there is no apparent mtDNA repair mechanism; therefore, there is a much higher mutation rate in mtDNA than in nuclear DNA. In fact, some regions of the mtDNA genome evolve at rates nearly 10 times that of a single-copy nuclear gene. These variable regions are of particular interest and value for human identity testing. Most of the sequence variation between individuals is found within two specific segments of the control region: hypervariable region 1 (HV1) and hypervariable region 2 (HV2) (Greenberg et al., "*Intraspecific Nucleotide Sequence Variability Surrounding The Origin Of Replication In Human Mitochondrial DNA*", Gene, 1983, 21:33-49). Typically, HV1 spans the region between nucleotides 16,024 and 16,365, and HV2 spans nucleotides 73 to 340. The small size of these two regions makes them particularly amenable to amplification by PCR; hence, HV1 and HV2 are routinely typed for forensic testing purposes.

As discussed above, mtDNA is maternally inherited (Case et al., "*Maternal Inheritance Of Mitochondrial DNA Polymorphisms In Cultured Human Fibroblasts*", Somat. Cell Genet., 1981, 7:103-108; Giles et al., "*Maternal Inheritance Of Human Mitochondrial DNA*", Proc. Natl. Acad. Sci. (USA), 1980, 77:6715-6719). Thus, barring mutation, the mtDNA sequence of siblings and all maternal relatives is identical. In fact, due to the lack of recombination in mtDNA, maternal relatives several generations removed from the test sample may still serve as reference samples (Ginther et al., "*Identifying Individuals By Sequencing Mitochondrial DNA From Teeth*", Nature Genetics, 1992, 2:135-138; Holland et al., "*Mitochondrial DNA Analysis Of Human Skeletal Remains: Identification Of Remains From The Vietnam War*", J. Forensic Sci., 1993, 38:542-553).

II. Nomenclature of mtDNA

The naming of mtDNA sequences is important for correct identification during forensic typing. As used herein, the term "naming" refers to the numbering used to describe the order of nucleotides in a nucleotide sequence, and the manner in which variations between two sequences are to be described. Naming the 600 bases necessary to describe the results from screening regions HV1 and HV2 is cumbersome; therefore, an alternate approach has been developed, that identifies only differences between a reference sequence and a query or sample sequence. Anderson et al were the first to sequence the entire mtDNA genome, and the published sequence is used as a reference standard, termed the Cambridge Reference Sequence (CRS) (Anderson et al., "*Sequence And Organization Of The Human Mitochondrial Genome*", Nature, 1981, 290:457-465). The sequence was updated by Anderson in 1999, and the new sequence is known as the revised Cambridge Reference Sequence (rCRS). (Andrews et al., "*Reanalysis And Revision Of The Cambridge Reference Sequence For Human Mitochondrial DNA*", Nature Genetics, 1999, 23:147) This sequence is displayed as the light strand sequence, and is compared directly to sample sequences. Only differences between the aligned samples and the rCRS are noted. For example, position number 16311 in the rCRS is listed as thymidine, or T; however, if an individual has a mutation at that position in which the T is substituted with a cytosine, or C, this polymorphism is designated 16311C. All other positions in the region sequenced are assumed to be identical to the rCRS. Insertions are designated by placing a period after the last aligned base in the Anderson sequence and listing the insertion with the appropriate nucleotide. For example, if the bases beyond position 16192 are out of register by one base due to, for example, insertion of a C, the inserted base is designated 16192.1C. If a C and a T are inserted, they are designated 16192.1C and 16192.2T. Deletions are recorded as the number of the base or bases missing with respect to the rCRS. For example, if nucleotide 75 is missing from the sample sequence, it is designated as 75D or 75−. If a base cannot be determined unambiguously, it is designated in accordance with appropriate IUPAC nomenclature (see below).

Naming mtDNA sequences in this manner provides a common language for describing variation observed in the human population. However, ambiguities do arise at times. Most of these ambiguities in alignment/nomenclature arise from misplaced insertions or deletions. Ambiguities in sequence alignments result in incorrect sequences being placed in reference population databases, which in turn affects the data available regarding the number of times the sample sequence is observed in a given population. As discussed above, Wilson et al (Wilson et al., "Recommendations For Consistent Treatment Of Length Variants In The Human Mitochondrial DNA Control Region", Forensic Sci. Int., 2002, 129:35-42; Wilson et al., "Further Discussions Of The Consistent Treatment Of Length Variants In The Human Mitochondrial DNA Control Region", 2002, Forensic Sci. Comm., 4:4) developed an approach to standardize alignments using differential weighting of transitions, transversions, insertions and deletions. The Wilson method provided recommendations for forensic scientists to assist them in interpreting and naming the mtDNA data generated. By utilizing this method, inconsistencies in nomenclature could be clarified, and from the higher quality databases generated by the use of this method, more reliable profile searches could be performed.

The "Wilson Rules" are as follows:
1. Characterize the variants using the least number of differences (i.e. substitutions, insertions, deletions) from the reference sequence.
2. If there is more than one possible alignment, each having the same number of differences with respect to the reference sequence, a prioritization is made first for insertions or deletions ("indels"), then transitions, and lastly, transversions.
3. Insertions and deletions should be placed 3' with respect to the light strand (when possible, insertions and/or deletions should be combined)
4. Gaps are combined only if they can all be placed in the most 3' position while maintaining the same number of differences from the reference sequence.
5. Bases designated as "N" do not affect the recommendations.
6. These recommendations are hierarchical. 1 is given precedence, followed by 2 and 3, etc.

III. Improved Methods for Analyzing DNA Sequence Data

The present invention uses a computer system and computer programming instructions to implement an alignment algorithm comprising a set of rules. The computer system may be discrete (e.g., a desktop computer, PDA, etc.), or may be virtual or networked with other computers. The computer system will comprise memory for storing the alignment algorithm computer programming instructions and sequence data and for storing the results of the implementation of the algorithm, a processor for accessing and implementing the rules of the algorithm, a data input means (for example, a keyboard, scanner, network interface to a sequencing device, to the internet, or to another computer device) and a display or printer for imparting the results of the analysis to users of the computer system.

In general overview, the present invention comprises alignment algorithm computer programming instructions that permit the computer system to generate a rough alignment of a reference sequence and a sample sequence and then to identify large regions in which the sequences match one another. The system and methods of the present invention use a standard implementation of the Smith-Waterman algorithm (Smith et al., "Identification Of Common Molecular Subsequences", 1981, Journal of Molecular Biology 147: 195-197) for this rough alignment. Regions between matching regions are then, by definition, polymorphic regions and the difference between the reference and sample in these polymorphic regions needs to be described with a type. The boundaries of the polymorphic regions are adjusted to provide proper contextual information about neighboring bases for use when aligning and typing the region. This adjustment can include expansion and subdivision. Expansion can take place, for example, when wishing to keep a repeated motif together. Subdivision occurs around the HV2 C-stretch in order to ensure alignment between specific landmarks.

Figure 2:
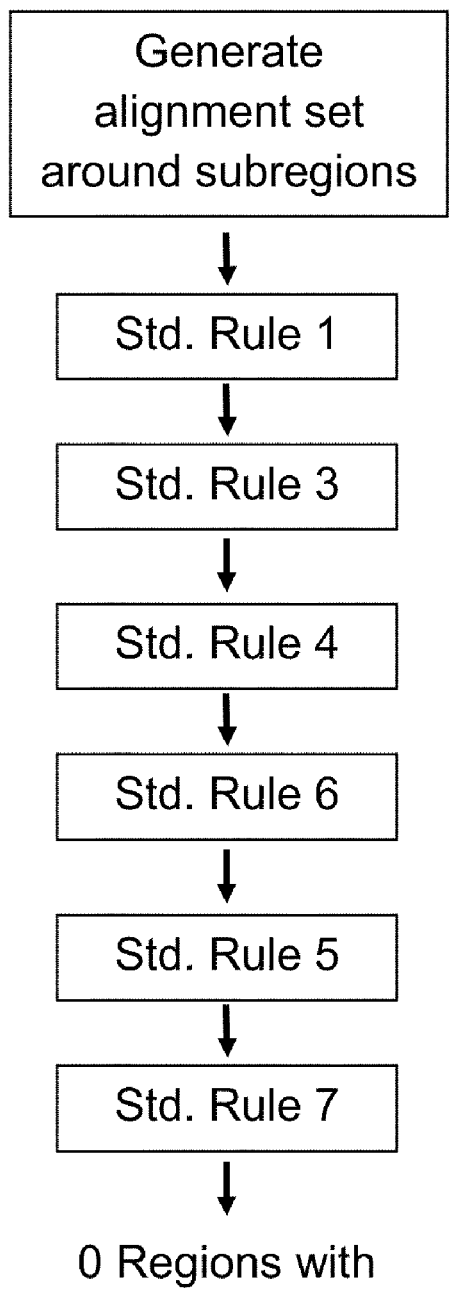
FIG. 2 shows a block diagram of the hierarchical method used by the system and methods of the present invention to sort possible alignment sequences present in the HV2CS region of the mitochondrial DNA (bases 300-316).

In each polymorphic region, the alignment algorithm computer programming instructions generates a set of possible alignments between the reference or query sequence and the sample sequence. In one embodiment of the invention, such set of possible alignments will contain every possible alignment between the reference/query sequence and the sample sequence. Alternatively, heuristic considerations (either computer software-based or computer hardware-based) may be employed to enhance the overall efficiency of the alignment algorithm instructions by identifying for subsequent processing a subset of the set of every possible alignments whose members exhibit greater potential compliance with the selection rules than other possible alignments in light of a specified criterion (see, Huang et al., "Accurate Anchoring Alignment Of Divergent Sequences", 2006, Bioinformatics, 22(1):29-34; Hulsen et al., "Testing Statistical Significance Scores Of Sequence Comparison Methods With Structure Similarity", 2006, BMC Bioinformatics, 7:444; Ilie et al., "Multiple Spaced Seeds For Homology Search", 2007, Bioinformatics, 23(22):2969-77; Manavski et al., "CUDA Compatible GPU Cards As Efficient Hardware Accelerators For Smith-Waterman Sequence Alignment", 2008, BMC Bioinformatics, 9 Suppl 2:S10; Rognes, T., "ParAlign: A Parallel Sequence Alignment Algorithm For Rapid And Sensitive Database Searches", 2001, Nucleic Acids Res., 29(7):1647-52; Rognes et al., "Six-Fold Speed-Up Of Smith-Waterman Sequence Database Searches Using Parallel Processing On Common Microprocessors", 2000, Bioinformatics, 16(8):699-706; Olsen et al., "Rapid Assessment Of Extremal Statistics For Gapped Local Alignment", 1999, Proc Int Conf Intell Syst Mol Biol., 211-22; Rognes et al., "SALSA: Improved Protein Database Searching By A New Algorithm For Assembly Of Sequence Fragments Into Gapped Alignments", 1998, Bioinformatics, 14(10):839-45) For example, such heuristic considerations may be used to preferentially process (i.e., perform an analysis upon subset members prior to analyzing alignments that are not members of the subset), focus on, or restrict analysis to that subset of all possible alignments of the sample sequence exhibiting at least 20% identity to the reference or query sequence, more preferably at least 30% identity to the reference or query sequence, still more preferably at least 40% identity to the reference or query sequence, more preferably still at least 50% identity to the reference or query sequence, more preferably still at least 60% identity to the reference or query sequence, more preferably still at 70% identity to the reference or query sequence, more preferably still at least 80% identity to the reference or query sequence, more preferably still at least 90% identity to the reference or query sequence, most preferably at least 95% identity to the reference or query sequence. This set of possible reference/query sequence to sample sequence alignments is processed by the computer system, applying each rule in series to select the compliant alignments in the set. The standard execution orders of the rules are shown in FIG. 1 and the modified procedure used for the region aligned to the rCRS 300 to 315 region is shown in FIG. 2. The heuristic considerations employed in the present invention preferably maintain complete accuracy of alignment (i.e., preferably there is no sacrifice of accuracy in order to satisfy the heuristic considerations).

Each rule of the alignment algorithm computer programming instruction is responsible for discarding all of the alignments in the regions' set of generated possible alignments that do not comply with the rule. If only one alignment remains after discarding the noncompliant alignments, that alignment is the solution and used to create the type description of the polymorphism(s) in that region. However after the computer system implements the rule, if more than one valid alignment still remains in the set of alignments for that region, then the alignment algorithm computer programming instructions direct that the set be passed to the next rule in the series for further processing.

In various embodiments, the present invention encompasses the incorporation of the methods of the invention into existing hardware or software-based analysis platforms or packages. Those of skill in the art will appreciate that the various methods disclosed herein may be implemented as electronic hardware, computer software, or combinations of both. The implementation of the methods of the present invention as hardware or software depends upon the desired application and design constraints imposed upon the system. A person of skill in the art may implement the present invention in varying ways, depending upon the application; however, such implementation does not constitute a departure from the scope of the system and methods of the present invention.

The various methods disclosed herein may be performed with a general purpose processor, a digital signal processor (DSP), an application-specific integrated circuit (ASIC), a field-programmable gate array (FPGA), or other programmable logic device, discrete gate, or transistor logic, discrete hardware components, or any combination thereof designed to perform the functions described herein. A general purpose processor may be a microprocessor, but may also be any processor, controller, microcontroller, or state machine. A processor may also be implemented as a combination of any of the aforementioned computing devices.

The steps of the methods of the present invention may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD or any other form of storage medium known in the art. A preferred storage medium is one in which the processor can read information from and write information to said storage medium. In another embodiment, the storage medium may be integral to the processor, and both may reside in an application-specific integrated circuit.

The system and methods of the present invention need not be limited exclusively to mtDNA sequence analysis; they may be integrated into consensus analysis approaches for DNA or RNA sequencing, or used with existing data to definitively type a nucleotide sequence. The methods described herein are able to be modified to utilize other rule sets useful for other analysis approaches.

A. Preferred Alignment Algorithm Computer Programming Instructions for Analyzing mtDNA Sequence Data: Standard Rules The alignment algorithm computer programming instructions of the present invention will preferably permit the computer system to implement the processing of reference, sample and query sequences in accordance with the following rules:

Rule 1. Least Number of Differences. The general principle for nomenclature rules is to select an alignment with the least number of differences between the rCRS and the sample consensus sequence (Wilson et al., "*Recommendations For Consistent Treatment Of Length Variants In The Human Mitochondrial DNA Control Region*", Forensic Sci. Int., 2002, 129:35-42; Wilson et al., "*Further Discussions Of The Consistent Treatment Of Length Variants In The Human Mitochondrial DNA Control Region*", 2002, Forensic Sci. Comm., 4:4). For each polymorphic region, the system and methods of the present invention first generate a set of possible alignments of the sample consensus in the region that have the minimum number of differences from the rCRS.

An ambiguous or heteroplasmically equivalent substitution in the sample consensus sequence is not considered a difference with the rCRS. The IUPAC nomenclature is used to determine heteroplasmic equivalence: A (Adenine), C (Cytosine), G (Guanine), T (Thymine), U (Uracil), R (A or G), Y (C or T), S (G or C), W (A or T), K (G or T), M (A or C), B (C or G or T), D (A or G or T), H (A or C or T), V (A or C or G), N (any base), "." or "-" (gap); A (Alanine), C (Cysteine), D (Aspartic Acid), E (Glutamic Acid), F (Phenylalanine), G (Glycine), H (Histidine), I (Isoleucine), K (Lysine), L (Leucine), M (Methionine), N (Asparagine), P (Proline), Q (Glutamine), R (Arginine), S (Serine), T (Threonine), V (Valine), W (Tryptophan), Y (Tyrosine). An inserted ambiguous base in the consensus sample sequence is counted as a difference from the rCRS.

Rule 2. Preserve the AC Motif in mtDNA Control Region. A polymorphism in the control region of mtDNA near positions 515-525 (ACACACACACC SEQ ID NO:1) of the rCRS has been characterized and determined to be a repeating "AC" motif (Bodenteich et al., "*Dinucleotide Repeat In The Human Mitochondrial D-Loop*.", Human Molecular Genetics, 1992, 1(2):140; Bodenteich et al., "*A Lifetime Of Retinal Light Exposure Does Not Appear To Increase Mitochondrial Mutations*.", Gene, 1991, 108(2):305-310). This motif appears in human populations in varying lengths, generally from 4 to 9 AC repeats. If the region includes the AC repeats (rCRS range 515-525) the system and methods of the present invention will select alignments that put insertions or deletions (indels) 3'-most and preserve the "AC" motif from those that place indels in less preferred positions. Example 1 compares a historical alignment with one generated using the present invention in which two deletions are placed together to reflect the deletion of one AC motif in the sample sequence, thus preserving the remaining ACs in the sequence. A person of skill in the art may implement this rule to include the preservation of additional repeating motifs that may be identified in genomic sequences from time to time.

Rule 3. Prefer Substitutions to Insertions or deletions ("Indels"). Polymorphisms in a sequence can be aligned by describing the difference in bases as a substitution or an indel. A substitution occurs when sequences are aligned so that one base is replaced with another in a sequence to describe the polymorphism. Insertions or deletions can also be used to describe the same polymorphism, by deleting the mismatched base and inserting the sequence base that is observed. Rule 3 dictates a preference for alignments achieved with substitutions rather than indels. The present invention chooses between two candidate alignments by selecting the alignment with the most substitutions.

Example 1 compares the method of the present invention, in which Rule 3 is applied and a preference for substitutions over indels is utilized to describe a polymorphism and contrasted to a historical alignment found in the Scientific Working Group on DNA Analysis Methods (SWGDAM) database. The historical alignment was achieved with three indels while the methods of the present invention alignment is achieved with two substitutions and one indel.

Rule 4. Prefer Transitions to Transversions. Nucleotide changes can be classified as transitions and transversions. Generally, transitions are more biologically feasible because the substituted nucleotides belong to the same chemical group, purine or pyrimidine. In contrast transversions involve nucleotide substitution across purine and pyrimidine chemical groups. The different chemical structures of these groups normally limit the occurrence of transversions.

Reflecting the fact that transitions are more biologically feasible than transversions this rule prefers the description of alignments between the reference and the sample sequence in which polymorphisms are described by transitions. Example 1 demonstrates a historical alignment in which the polymorphic region is described by an indel 56.1-C, a transition 73 A G, and a transversion, 57 T G. The methods of the present invention instead select an alignment that described the polymorphisms with an indel and two transitions; shown as the Rule 4 sequence alignment in Example 1. This rule is implemented by selecting between two candidate alignments the alignment with the most transitions. Thus, the alignment that is most biologically feasible is favored.

Rule 5. Place Insertions or deletions Contiguously When Possible. Indels can often be placed in several locations in order to align polymorphic sequences. The preferred alignment for nomenclature consistency places the indels in continuous groups as much as possible. Example 1 compares a historical type and a preferred alignment in which the same three indels are placed contiguous to one another.

Rule 6. Place Insertions or deletions 3' to Homopolymeric Stretches of DNA. For any choice of indel placement, the methods of the present invention prefer the indel position that preserves homopolymeric stretches and repeated neighboring patterns of base sequence and is on the 3' end of the homopolymeric stretch. The distinction between repeated motif and homopolymeric stretch can be important when refining a rough alignment into mismatch regions. For example, the region 98-114 of human mitochondrial DNA NC_001807.4 has the sequence: CTGGAGCCGGAG-CACCC (SEQ ID NO:41). The 100-110 region of this polynucleotide sequence thus consists of a fivemer (GGAGC), a C is present at position 105, followed by a repeat of the fivemer (GGAGC). When the 105 C and one of the fivemer occurrences is missing, as in 105-110d (Samples USA.335.000133, USA.HIS.000378 and USA.HIS.000499), it can be aligned in several ways:

```
Master Sequence   CTGGAGCCGGAGCACCC   (SEQ ID NO: 41)

Alignment (1)     CTGGAGC------ACCC   typed as
                                      105-110d Alignment (2)     CT------GGAGCACCC   typed as
                                      100-105d Alignment (3)     CTGGAGC---A-C-CC-   typed as 105d,
                                      106d, 107d,
                                      109d, 111d, 114d
```

If the refinement process did not seek to keep together the rCRS pair of GGAGC, the Smith Waterman placement of indels could be incorrectly taken at face value since everything else around it matches. Such a result, however, would be a nonforensic alignment. Rule 6 operates to make Alignment (1) the preferred alignment. Example 1 compares a historical alignment in which indels were not placed 3' to a homopolymeric stretch along with a preferred alignment that complies with this rule.

Rule 7. 3' Most Insertions and Deletions Tiebreaker Rule. It is possible for the set of alignments for each region to be down selected by all the rules and still have multiple valid candidate alignments remaining. Rule 7 implements the general 3' preference in these and all nomenclature rules as a tiebreaker to select the single preferred alignment for each region. For a set of alignments to reach this point, each alignment must have the same number of indel groups and not have both insertions and deletions in exactly the same positions in any two alignments.

Therefore, a preferred embodiment of the present invention comprises a method of aligning a sample mtDNA sequence with a reference mtDNA sample by applying the hierarchical steps of: (a) choosing the alignment(s) with the fewest number of differences from the reference sequence; (b) choosing the alignment(s) that preserve the AC motif at rCRS region 515-525; (c) choosing the alignment(s) that contain substitutions rather than insertions or deletions; (d) choosing the alignment(s) that contain transitions rather than transversions; (e) choosing the alignment(s) that place insertions or deletions contiguously; (f) choosing the alignment(s) that place insertions or deletions 3' to any homopolymeric stretches present in the sequence; and (g) choosing the alignment with the insertion/deletion at the 3'-most point in the sequence.

Example 1 shows two alignments of the sample sequence that are compliant with all previous rules applied to down select the set of alignments. The insertion tiebreaker rule leads to the selection of the alignment with an insertion at 16193 over the alternative alignment that placed an insertion at position 16188. To illustrate the tiebreaker rule using alignments of sample sequences that use 3' deletion preferences, Example 1 compares historical data with that generated by the system and method of the present invention, and shows that application of Rule 7 leads to the selection of the alignment with a deletion at 16189 over the historical alignment that placed the deletion at position 16188.

B. Preferred Alignment Algorithm Computer Programming Instructions for Analyzing mtDNA HV2 C-Stretch (HV2CS) Sequence Data: HV2CS Rules The region of mtDNA spanning residues 299-315 (SEQ ID NO:2 (AAACCCCCCCTCCCCC) contains the HV2 C-Stretch (HV2CS) and presents unique challenges to investigators attempting to align sequences in this region due to the presence of five cytosine residues in the rCRS in the HV2 region from positions 311 to 315 that represents a rare polymorphism from the majority of the population that has six cytosines in this poly-cytosine stretch (Andrews et al., *"Reanalysis And Revision Of The Cambridge Reference Sequence For Human Mitochondrial DNA"*, Nature Genetics, 1999, 23:147). As a result almost 99% of the samples in the SWGDAM database (4834 of the 4838 samples tested) have a 315.1 C type in this region.

Due to the fact that the vast majority of the database population has six cytosines from 311-315.1C in mtDNA region HV2, the computer-facilitated system and methods of the present invention incorporate this data into a new set of alignment algorithm computer programming instructions that implement rules, specific for this particular region of mtDNA. HV2CS Rule 1 applies a preference for aligning the thymine at the 310 position (the 310T) in the rCRS with a thymine residue in the sample sequence and preserving the statistically-likely 315.1 C type description for polymorphisms in this region. Example 2 shows a sequence found the SWGDAM database typed according to HV2CS Rule 1 (CHN.ASN.000451). Using the methods of the present invention, this sample sequence is described with two insertions and a deletion, including a 315.1C, which preserves the 310T alignment. The rules for typing of sequences in the mtDNA HV2CS region differ from those of the Standard Rules (FIG. 1), in that the Standard Rules would produce a preferred alignment, shown in Example 1, that has two differences from the rCRS ("308 C T" and "3310 T–"), which meets the "least number of differences" criterion in Rule 1. The modified rules for typing mtDNA HV2CS regions are shown in FIG. 2.

In addition to the poly-C stretch present in this region of mtDNA, analysis of the SWGDAM data also revealed a historical preference for aligning the 300 to 302 poly-A region and the 303 to 309 poly-C region in the rCRS with matching regions in the sample sequence. This preference is also incorporated into alignment algorithm computer programming instructions for implementing HV2CS Rule 1, sorting possible alignments according to a preference for preserving these regions when aligning sample sequences. Example 2 shows the sequence from CHN.ASN.000451 with the preferred alignment produced by application of the methods of the present invention.

The alignment algorithm computer programming instructions HV2CS rules begin by directing the isolation of this region (300-315.1C) from the sample sequence and generating a set of alignments between the sample and the reference in the region that align the rCRS 310T with the candidate thymine(s) in the sample sequence and also aligns the poly-A region 299-300 and 302-303 boundaries, the 303-304 and 309 boundaries and the ending 315-316 boundary in the reference with the corresponding candidate boundaries in the sample sequence. When the boundaries of these regions cannot be found (most critically the 299-300 boundary) then the methods of the present invention will find that this region cannot be typed using the regular rules. However, such regions may still be typed in accordance with the present invention, as discussed below (e.g., in Example 7).

Isolating the region in the sample sequence that matches the rCRS 300 to 315 sequence and isolating the boundaries within this region is a computationally challenging task. An illustrative computational procedure is described in Example 7.

Each alignment in the set generated by the methods of the present invention will reflect the application of HV2CS Rule 1, aligning T residues and the poly-A and poly-C boundaries. This set of alignments is then down-selected by sequential application of the typing rules applied in the order illustrated in FIG. 2. Each rule is responsible for discarding all of the alignments in the regions' set of generated possible alignments that do not comply with the rule.

When typing the HV2CS, the order in which the alignment algorithm computer programming instructions for the Standard Rules are applied is different. This change preserves the statistically-likely placement of the sixth C after the 310T as 315.1C in the event that there is a second indel in the sample in the 310 to 315 subregion of the HV2CS. A further embodiment of the present invention therefore comprises a computer-facilitated method of aligning a sample mtDNA sequence containing HV2CS with a reference mtDNA sample containing HV2CS in which alignment algorithm computer programming instructions implement the hierarchical steps of: (a) preserving the 300-315.1C sequence; (b) choosing the alignment(s) with the minimum number of differences from the rCRS; (c) choosing the alignment(s) containing substitutions rather than insertions or deletions; (d) choosing the alignment(s) that contain transitions rather than transversions; (e) choosing the alignment(s) with insertions or deletions 3' to any homopolymeric stretches in the sequence; (f) choosing the alignment(s) that place insertions or deletions contiguously; and (g) choosing the alignment that contains the 3'-most insertion or deletion.

Having now generally described the invention, the same will be more readily understood through reference to the following examples, which are provided by way of illustration and are not intended to be limiting of the present invention unless specified.

EXAMPLES

Example 1

Comparison of Current mtDNA Alignment Results with Results Obtained Using the Standard Rules of the Present Invention The computer-facilitated system and methods of the present invention relate to improving mtDNA sequence analysis by reducing inconsistencies in typing. The present invention, by automating and utilizing the disclosed method in which a set of possible alignments are generated and subjected to a hierarchical set of rules until only one possible alignment remains, will greatly reduce the number of database inconsistencies. The following examples illustrate instances in which database inconsistency was found, and compare them to the manner in which the computer-facilitated methods of the present invention analyze the sequence data.

Rule 1. Least Number of Differences. In accordance with the alignment algorithm computer programming instructions of a preferred embodiment of the present invention, a first rule is implemented to the set of possible alignment sequences which results in the selection of the alignment that contains the fewest differences from the rCRS. To illustrate the application of this rule, homopolymeric stretches of Cs with a T within the stretch that can be found in some individuals at positions 16180-16193 are used. In this example, comprising positions 16180-16198, the T is at position 16186 rather than at 16189 as in the reference sequence. Additionally, the total number of bases between positions 16180 and 16193 is less than the 14 present in the CRS.

```
5' AAAACCTCCCCCCATGCT 3'      Sample   (SEQ ID NO: 3)

5' AAAACCCCCTCCCCATGCT 3'     rCRS     (SEQ ID NO: 4)
```

Three possible alignments may result:

```
1. 5' AAAACCTCC-CCCCATGCT 3'   Sample (SEQ ID NO: 5)

5' AAAACCCCCTCCCCATGCT 3'   rCRS   (SEQ ID NO: 6)

2. 5' AAAACC-TCCCCCCATGCT 3'   Sample (SEQ ID NO: 7)

5' AAAACCCCCTCCCCATGCT 3'   rCRS   (SEQ ID NO: 8)

3. 5' AAAACCTCCCCCC-ATGCT 3'   Sample (SEQ ID NO: 9)

5' AAAACCCCCTCCCCATGCT 3'   rCRS   (SEQ ID NO: 10)
```

According to the methods of the present invention, the alignment algorithm computer programming instructions operate to choose the first alignment, as it contains the least number of differences between the sample sequence and the reference sequence. In this particular example the historical methods previously described and those of the present invention result in the same choice of alignment.

Rule 2. Preservation of AC Motif. From the remaining alignments after application of Rule 1, if the region includes the AC repeats described above (rCRS range 515-525), the computer system and computer-facilitated methods of the present invention will select alignments that put insertions or deletions ("indels") 3'most and preserve the "AC" motif over those that place indels in less preferred positions. This is in contrast to the historical practice, which gives preference to 3' indels over preserving the AC motif. Previously, the rCRS sequence 514-525 had been aligned with a sample sequence as follows:

```
                            (SEQ ID NO: 11)
    rCRS 514-525    5' AGCACACACACACCGC 3'

(SEQ ID NO: 12)
    USA.HIS.00093   5' AGCACACACAC-C-GC 3'
```

Applying Rule 2 of the present method results in the following sequence alignment:

```
                            (SEQ ID NO: 13)
    rCRS 514-525    5' AGCACACACACACCGC 3'

(SEQ ID NO: 14)
    Rule 2          5' AGCACACACAC--CGC 3'
```

Rule 3. Prefer Substitutions to Insertions or Deletions. After discarding possible alignments that do not meet the requirements of Rules 1 and 2, remaining sequence alignment possibilities are subjected to the further limitation of a preference for substitutions over indels. Previously, the rCRS sequence 16178 to 16193 had been aligned with a sample sequence by deleting 16183 A and inserting two Cs at 16193 and 16194 as follows:

```
                            (SEQ ID NO: 15)
    rCRS 16178-16193   5' TCAAAACCCCCTCCCC 3'

(SEQ ID NO: 16)
    USA.AFR.000537     5' TCAAA-CCCCCTCCCCCC 3'
```

In contrast, Rule 3 of the present invention results in the following sequence alignment, utilizing two substitutions (16183A C, 16189T C) and one insertion (16187.1T):

```
                            (SEQ ID NO: 17)
    rCRS 16178-16193   5' TCAAAACCCC-CTCCCC 3'

(SEQ ID NO: 18)
    Rule 3             5' TCAAACCCCCTCCCCCC 3'
```

Rule 4. Prefer Transitions to Transversions. If multiple sequence alignments are present after application of Rules 1-3, the computer-facilitated method described herein calls for a preference to be given to transitions over transversions. Remaining alignment possibilities will be sorted accordingly. Previously, the rCRS sequence 54 to 75 had been aligned with a sample sequence using an indel (56.1 C), a transition (73 A G), and a transversion, (57 T G) as follows:

```
                            (SEQ ID NO: 19)
    rCRS 54-75      5' TA-TTTCGTCTGGGGGGTATG 3'

(SEQ ID NO: 20)
    USA.350.000004  5' TACGTTTCGTCTGGGGGGTGTG 3'
```

Rule 4 of the present invention results in the following sequence alignment, instead selecting an alignment that uses an indel (57.1G) and two transitions (56C, 73G):

```
                            (SEQ ID NO: 21)
    rCRS 54-75      5' TAT-TTTCGTCTGGGGGGTATG 3'

(SEQ ID NO: 22)
    Rule 4          5' TACGTTTCGTCTGGGGGGTGTG 3'
```

Rule 5. Place Insertions or Deletions Contiguously When Possible. Multiple sequence alignment possibilities remaining after application of Rules 1-4 will then be subject to a preference for contiguous indel placement. Previously, the rCRS sequence 451 to 460 had been aligned with three indels (455.1T, 455.2T, 459.3C) as follows:

```
rCRS 451-460   5' ATTTT--CCCC-T 3'   (SEQ ID NO: 23)

EGY.AFR.000035 5' ATTTTTTCCCCCT 3'   (SEQ ID NO: 24)
```

Rule 5 of the present invention results in the following sequence alignment, instead selecting an alignment that aligns all three indels contiguously (455.1T, 455.2T, 455.3C):

```
rCRS 451-460  5' ATTTT---CCCCT 3'   (SEQ ID NO: 25)

Rule 5        5' ATTTTTTCCCCCT 3'   (SEQ ID NO: 26)
```

Rule 6. Place Insertions or Deletions 3' to Homopolymeric Stretches. In practice, it is generally preferred that homopolymeric stretches of sequence be preserved during alignment, if possible, by placing any indels 3' to these stretches. Therefore, any remaining sequence alignment possibilities after application of Rules 1-5 will be sorted according to this preference. Alignments that do not preserved homopolymeric stretches will be discarded. Previously, the rCRS sequence 16170 to 16183 had been aligned with a sample sequence such that the indel was not placed 3' to the homopolymeric stretch, and thus did not preserve the homopolymeric stretch:

```
                            (SEQ ID NO: 27)
    rCRS 16170-16183   5' AATCCACATCAAAA 3'

(SEQ ID NO: 28)
    SKE.AFR.000060     5' AACCCACATC-AAA 3'
```

Rule 6 of the present invention results in the following sequence alignment, instead selecting an alignment that places the indel 3' of the homopolymeric stretch.

```
                            (SEQ ID NO: 29)
    rCRS 16170-16183   5' AATCCACATCAAAA 3'

(SEQ ID NO: 30)
    Rule 6             5' AACCCACATCAAA- 3'
```

Rule 7. Tiebreaker Rule: 3' Most Insertions and Deletions. If Rules 1-6 have been implemented, and multiple alignment possibilities still exist, preference is given for those alignments that place insertions or deletions 3'-most. The following is a historical example in which the insertion (16188.1C) was not placed 3'-most:

```
                            (SEQ ID NO: 31)
    rCRS 16180-16194   5' AAAACCCCC-TCCCC 3'
```

-continued

```
                                            (SEQ ID NO: 32)
USA.AFR.000222      5' AAACCCCCCCCCCC 3'
```

In contrast, Rule 7 of the present invention results in the following sequence alignment, instead selecting an alignment that places the indel (16194.1 C) 3'-most:

```
                                            (SEQ ID NO: 33)
rCRS 16180-16194    5' AAAACCCCTCCCC- 3'

(SEQ ID NO: 34)
Rule 7              5' AAACCCCCCCCCCC 3'
```

Conversely, deletions also may be placed 3'-most in order to reduce the number of compliant alignments. The following is an historical example in which this practice was not followed, and the deletion was placed at 16188:

```
                                            (SEQ ID NO: 35)
rCRS 16180-16194    5' AAAACCCCTCCCCA 3'

(SEQ ID NO: 36)
USA.AFR.000291      5' AAAACCCC-ACCCCA 3'
```

Once again, Rule 7 dictates that the deletion be placed as far to the 3' side of the sequence as possible to eliminate multiple alignments. The following is an example of the tiebreaker rule as it applies to deletions, where the deletion is placed at 16189:

```
                                            (SEQ ID NO: 37)
rCRS 16180-16194    5' AAAACCCCTCCCCA 3'

(SEQ ID NO: 38)
USA.AFR.000291      5' AAAACCCCA-CCCCA 3'
```

Example 2

Methods for Analyzing mtDNA HV2CS Sequence Data Using the HV2CS Rules of the Present Invention As described above, the HV2CS region from positions 311 to 315.1C in the majority of the population has six cytosines in this poly-cytosine stretch. By the alignment algorithm computer programming instructions placing a T at position 310, the preservation of the 311-315.1C cytosine stretch is maintained. Additionally, analysis of the SWGDAM data revealed a historical preference for aligning the 300 to 302 poly-A region and the 303 to 309 poly-C region in the rCRS with matching regions in the sample sequence Therefore, the standard rules, as described in Example 1, have been modified for use in analyzing mtDNA HV2CS sequence data as follows. The alignment algorithm computer programming instructions operate to implement the following HV2CS rules.

HV2CS Rule 1. Preserve SEQ ID NO:2 (AAAC-CCCCCCTCCCCC). Each alignment in the set generated by the methods and system of the present invention will align the 310 T (shown in heavy underline) residues and the poly-A and poly-C boundaries (shown in dotted underline), as well as preserve the six cytosine residue sequence from 311-315.1C (shown in double underlined).

```
                                            (SEQ ID NO: 39)
rCRS 295-317    5' CCACCAAACCCCCCC-TCCCCC-GC 3'

(SEQ ID NO: 40)
HV2 Rule 1      5' CCAC-AAACCCCCCCCTCCCCCCGC 3'
```

This is a departure from the alignment algorithm computer programming instructions for the Standard Rules described in Example 1, in that the minimum number of differences rule is not applied first.

HV2CS Rule 2. Minimum Number of Differences. As described in Example 1, Rule 1, the alignment sequence with the fewest differences from the rCRS is chosen from the remaining alignments after application of HV2CS Rule 1.

HV2CS Rule 3. Prefer Substitutions to Insertions or Deletions. As described in Example 1, Rule 3, after applying HV2CS Rules 1 and 2 to the set of possible sequence alignments, if multiple alignment possibilities still exist, HV2CS Rule 3 states that preference will be given to those alignments that contain substitutions rather than indels.

HV2CS Rule 4. Prefer Transitions to Transversions. As described in Example 1, Rule 4, if multiple sequence alignments exist after the application of HV2CS Rules 1-3, then those remaining alignments will be sorted according to a preference for transitions over transversions.

HV2CS Rule 5. Place Insertions or Deletions 3' to Homopolymeric Stretches. As described in Example 1, Rule 6, remaining alignments after application of HV2CS rules 1-4 will be further sorted by applying the preference for placing indels 3' to homopolymeric sequence stretches.

HV2CS Rule 6. Place Insertions or Deletions Contiguously When Possible. As described in Example 1, Rule 5, after applying Rules 1-5 to the possible alignments under consideration, if multiple alignments are still possible, HV2CS Rule 6 calls for the remaining possibilities to be sorted according to a preference for contiguous placement of indels.

HV2CS Rule 7. Tiebreaker Rule: 3' Most Insertions and Deletions. As a final step, any remaining multiple alignments are subjected to HV2CS Rule 7, which is the same as the Standard Rule 7. Preference is given to alignments which place indels 3'-most in the sequence.

Example 3

Congruence of Methods of the Present Invention Results and Historical Types In the SWGDAM Data Set The computer system and computer-facilitated methods described by the present invention were generated to automate the historical procedure of selecting forensic alignments and generating types for forensic use. Guidelines for this process were informally called "the Wilson Rules" (Wilson et al., "Recommendations For Consistent Treatment Of Length Variants In The Human Mitochondrial DNA Control Region", 2002, Forensic Sci. Int.129(1):35-42.).

The system and methods of the present invention were developed using 4839 samples in the SWGDAM mtDNA population database as the historical reference (Monson et al., "The mtDNA Population Database: An Integrated Software and Database Resource for Forensic Comparison", 2002, Forensic Science Communications, 4(2)). Consensus sequences were generated for each sample by applying the sample's type to the rCRS in the range 15998-576. These consensus sequences were analyzed using the system and methods of the present invention, which produced a rule-compliant type for each sample. The rule-compliant type was compared to the historical type for analysis.

In these SWGDAM samples, there were 40,357 polymorphic regions that contained one or more differences from the rCRS. Of the 40,357 polymorphic regions with one or more differences from the rCRS, 32,915 had only one possible alignment between the sample and the rCRS after applying Rule 1, which involves searching for alignments that contain the minimum number of differences between the sample sequence and the rCRS. The remaining 7420 regions (in 4802 samples) had polymorphic regions with multiple possible alignments and the same minimum number of differences, and therefore required application of later rules. After re-typing the samples using the system and methods of the present invention, only 33 regions in 33 samples differed from the historical types, which is 99.92% consistent with the manual typing procedure used to generate the database.

Example 4

Independent Validation Testing

An additional 1,254 samples that were not processed or typed were used as an independent validation data set. Using the computer system and computer-facilitated methods of the present invention, only 56 polymorphisms in 20 regions of mtDNA out of a total of 11,303 polymorphisms were found to differ from the historical types. The low 0.18% discrepancy rate is similar to the rate achieved in the SWGDAM data set, and indicates that the rules provide accurate, reliable results.

Example 5

Comparison of Results from EMPOP Database with Those Generated by the Present Invention The EMPOP (Parson et al., "*The EDNAP Mitochondrial DNA Population Database (EMPOP) Collaborative Exercises: Organisation, Results and Perspective*", 2004, Forensic Sci. Int., 139(2-3):215-26) database contains 5,173 mtDNA control region haplotypes from all over the world. In keeping with convention, the consensus sequences of the mtDNA samples are described by their differences to the rCRS. Recent work reports that alignment and nomenclature rules to describe the difference from rCRS are derived phylogenetically (Bandelt et al., "*Consistent Treatment Of Length Variants In The Human MtDNA Control Region: A Reappraisal*", 2008, Int. J. Legal Med., 122(1):11-21).

The 5,173 control region sequences were analyzed using the system and methods of the present invention and the types were compared to the mtDNA profile used to describe that sequence on the EMPOP database. In total., only 24 differences in sequence typing between the data generated by the present invention and those found in the EMPOP database were discovered. To further emphasize the need for a consistent, reliable, computer-facilitated means for analyzing mtDNA sequence, four examples were found in the EMPOP database in which the same polymorphic sequence was given a different alignment in different samples.

Example 6

Variability Testing

The robustness and reliability of the computer system and computer-facilitated methods of the present invention were tested on over sixty million computer-generated sample sequences. Each test sample sequence was generated by introducing a random number of mutations (between 1 and 30) to the reference sequence region from 16025 to 525. The modification location is random with an equal distribution across the sequence and the modification is randomly chosen with an 80% chance of being a substitution and 10% chance each of insertion and deletion. One additional heteroplasmic modification is inserted at a random location by replacing the base with a symbol in the set "K", "M", "R", "D", "S", "H", "W", "V", "Y", "B", or "N". In every case, the system and methods of the present invention returned a type description that accurately described the computer-generated polymorphisms that had been randomly introduced to the reference sequence.

Example 7

Illustrative Code Showing the Function Performed by the Various Software Programs That May be Integrated into the Described Computer-Facilitated Method for DNA Alignment Isolate the HV2CS 300-315 region for special processing; identify 299-300 boundary and 315-316 boundary.
a) Identify 315/316 (3') boundary
   a. Examine the reference value to the immediate 3' of 315
      i. Find the position of the first nongap reference value 3' of 315
      ii. Set boundary3' to end of the region if out of bases
b) Attempt to identify 299-300 (5') boundary
   a. Examine consensus values aligned to reference positions 300, 301, 302
      i. Are any identical to 'A'?
         1. Yes—select the 5'most as the 5' beachhead position
         2. No—Are any IUPAC-equivalent to 'A'?
            a. Yes—select the 5'most as the 5' beachhead position
            b. No—set 5' beachhead position to −1
c) Was a 5' beachhead found?
   a. When a beachhead into the 300-302 region is found in the consensus, extend it to 3' and 5' to include any plausible bases.
      i. Examine the consensus value in the position immediately 5' to the 5' beachhead region. Include it in the region if
         1. it is a gap, or
         2. it is equivalent to an A, or
         3. it is not equivalent to a C
      ii. Continue i) until no more values are to be included 5'
         1. This means the beginning of the region was found, or
         2. A value equivalent to C but not A was found
      iii. Look for the 300/303 A/C boundary. Examine the consensus value in the position immediately 3' to the 5' beachhead region. Include it in the region if
         1. it is a gap, or
         2. it is equivalent to an A, or
         3. it is not equivalent to a C
      iv. Continue i) until no more values are to be included 3'
         1. This means that the end of the region was found, or
         2. A value equivalent to C but not A was found
   b. For an identified 300-302 beachhead, are different 299-300 boundary breaks possible within it?
      i. If the region has more than three bases, consider potential boundary breaks before and after each base, otherwise ii. If a base is not a gap and is not an A, consider potential boundary breaks before the value as well as after the value;
c. For each possible 299-300 boundary start, separate the region into sets with each subregion and its typing rules
   i. Are there any T's possible before the 3'boundary?
      1. Yes
         a. For each possible T, create a set of subregions such that
            i. The subregion 5' to the 299-300 boundary start is to be typed "Regular rules"
            ii. The subregion 299-300 boundary to the T is to be typed "HV2CSS rules"
            iii. The subregion 310T is to be typed to the possible T, "HV2CSS rules"
            iv. The subregion from the 310T/possible T to the 3' boundary is to be typed "HV2CSS rules"
            v. The subregion 3' to the 3' boundary is to be typed "regular rules"
      2. No
         a. Create a set of subregions such that
            i. The subregion 5' to the 299-300 boundary start is to be typed "Regular rules"
            ii. The subregion 299-300 boundary to the 3' boundary is to be typed "HV2CSS rules"
            iii. The subregion 3' to the 3' boundary is to be typed "regular rules"
d. For each set of subregions, run the set and total the number of differences produced by each set. Select the set with the least number of differences w.r.t. rCRS
   i. There is no tiebreaker mechanism at this level
   ii. The "if different by 2 or more" etc rules are not in place
e. Report that set as the HV2CSS result for the region d) No 5' beachhead found. This means that it is not possible to determine where to start using the HV2CSS typing rules and where to use the regular rules. The software makes another attempt at recovery.
   i. Are there any T's possible before the 3'boundary?
      1. Yes
         a. For each possible T, create a set of subregions such that
            i. The subregion 5' to the 299-300 boundary start to the T is to be typed "Regular rules"
            ii. The subregion 310T is to be typed to the possible T, "HV2CSS rules"
            iii. The subregion from the 310T/possible T to the 3' boundary is to be typed "HV2CSS rules"
            iv. The subregion 3' to the 3' boundary is to be typed "regular rules"
      2. No
         a. Use the original alignment, e.g. a single region that is aligned "regular rules" throughout.

Each publication, patent application and patent referred to within this disclosure is herein incorporated in its respective entirety. Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

---

What is claimed is:

1. A method for determining an optimal alignment between a first polynucleotide sequence (I) and second polynucleotide sequence (II), wherein said method employs a device that is programmed to perform steps comprising:

(A) receiving said sequences (I) and (II) into memory and processing said received sequences to generate a set of possible alignments between said sequences;

(B) applying an initial alignment rule to said set of possible alignments in order to select a set of compliant alignments from said set of possible alignments, wherein a compliant alignment is a possible alignment that complies with said applied initial alignment rule and wherein said initial alignment rule is a member of a hierarchical set of alignment rules composed of the initial alignment rule and one or more hierarchically ordered additional alignment rules, and wherein said additional alignment rules comprise a rule preferring a nucleotide substitution instead of a nucleotide insertion or deletion;

(C) (1) where the set of compliant alignments contains only a single compliant alignment, designating said single compliant alignment as said optimal alignment; or (2) where the set of compliant alignments contains more than one compliant alignment, applying the next additional alignment rule from the hierarchical set of alignment rules to said set of compliant alignments, removing alignment(s) that do not comply with said applied next additional alignment rule from the set of compliant alignments, and repeating step (C); and (D) reporting said optimal alignment.

2. The method of claim 1, wherein at least one of said sequences (I) and (II) is a sample sequence or a reference sequence.

3. The method of claim 1, wherein said polynucleotides having sequences (I) and (II) are mtDNA.

4. The method of claim 3, wherein said polynucleotides having sequences (I) and (II) comprise HyperVariable Region 2 C-Stretch (HV2CS) mtDNA sequences.

5. The method of claim 4, wherein said initial alignment rule maximally preserves the HV2CS sequence AAAC-CCCCCCTCCCCC (SEQ ID NO:2) and also maximally preserves the TCCCCC region of the HV2CS sequence.

6. The method of claim 5,
wherein said additional alignment rules comprise the following rules arranged hierarchically in the following order:
(1) a rule which selects the possible alignments with the lowest number of differences between sequence (I) and sequence (II);
(2) the rule preferring a nucleotide substitution instead of a nucleotide insertion or deletion;
(3) a rule preferring a transition substitution instead of a transversion;
(4) a rule that places insertions or deletions 3' to a homopolymeric stretch present in said sequences (I) and (II);
(5) a rule in which insertions or deletions are placed contiguously; and
(6) a rule in which insertions or deletions are placed 3'-most.

7. The method of claim 5, wherein said hierarchical set of alignment rules comprises
at least one additional hierarchically ordered alignment rule selected from the group consisting of:
(1) selecting the possible alignments with the lowest number of differences between sequence (I) and sequence (II);
(2) selecting those alignments containing transitions rather than transversions;
(3) selecting those alignments which place insertions or deletions 3' to any homopolymeric stretches present in said sequences (I) and (II);
(4) selecting those alignments in which insertions or deletions are placed contiguously; and
(5) selecting those alignments in which insertions or deletions are placed 3'-most.

8. The method of claim 1, wherein, in said step (A), said set of possible alignments contains a subset of the set of every possible alignment between said sequences (I) and (II).

9. The method of claim 1, wherein, in said step (A), said set of possible alignments contains every possible alignment between said sequences (I) and (II).

10. The method of claim 1, wherein said additional alignment rules comprise a rule which maximally preserves an AC motif of the polynucleotide sequence and locates any insertions or deletions 3' to the AC motif, wherein the AC motif is ACACACACACC (SEQ ID NO:1).

11. The method of claim 1,
wherein said initial alignment rule comprises selecting from said set of possible alignments the possible alignments with the lowest number of differences between sequence (I) and sequence (II) and eliminating all other alignments from said set of possible alignments; and
wherein said additional alignment rules comprise at least one rule selected from the group consisting of:
(1) a rule which maximally preserves an AC motif of the polynucleotide sequence and locates any insertions or deletions 3' to the AC motif, wherein the AC motif is ACACACACACC (SEQ ID NO:1);
(2) a rule preferring a transition substitution instead of a transversion;
(3) a rule in which insertions or deletions are placed contiguously;
(4) a rule that places insertions or deletions 3' to a homopolymeric stretch present in said sequences (I) and (II); and
(5) a rule in which insertions or deletions are placed 3'-most.

12. The method of claim 1,
wherein said initial alignment rule comprises selecting from said set of possible alignments the possible alignments with the lowest number of differences between sequence (I) and sequence (II) and eliminating all other alignments from said set of possible alignments; and
wherein said additional alignment rules comprise the following rules arranged hierarchically in the following order:
(1) a rule which maximally preserves an AC motif of the polynucleotide sequence and locates any insertions or deletions 3' to the AC motif, wherein the AC motif is ACACACACACC (SEQ ID NO:1);
(2) the rule preferring a nucleotide substitution instead of a nucleotide insertion or deletion;
(3) a rule preferring a transition substitution instead of a transversion;
(4) a rule in which insertions or deletions are placed contiguously;
(5) a rule that places insertions or deletions 3' to a homopolymeric stretch present in said sequences (I) and (II); and
(6) a rule in which insertions or deletions are placed 3'-most.

13. A computer system for determining an optimal alignment between a first polynucleotide sequence (I) and second polynucleotide sequence (II) comprising:
memory for storing alignment algorithm computer programming instructions and sequence data and for storing the results of the implementation of the alignment algorithm,
a processor for accessing and implementing the rules of the algorithm;
input means; and
means for imparting the results of the analysis to users of the computer system,
wherein said alignment algorithm computer programming instructions comprise instructions for causing said computer system to perform the steps of:
(A) receiving said sequences (I) and (II) into memory and processing said received sequences to generate a set of possible alignments between said sequences;
(B) applying an initial alignment rule to said set of possible alignments in order to select a set of compliant alignments from said set of possible alignments, wherein a compliant alignment is a possible alignment that complies with said applied initial alignment rule and wherein said initial alignment rule is a member of a hierarchical set of alignment rules composed of the initial alignment rule and one or more hierarchically ordered additional alignment rules, and wherein said additional alignment rules comprise a rule preferring a nucleotide substitution instead of a nucleotide insertion or deletion
(C) (1) where the set of compliant alignments contains only a single compliant alignment, designating said single compliant alignment as said optimal alignment; or
(2) where the set of compliant alignments contains more than one compliant alignment, applying the next additional alignment rule from the hierarchical set of alignment rules to said set of compliant alignments, removing alignment(s) that do not comply with said applied next additional alignment rule from the set of compliant alignments, and repeating step (C); and (D) reporting said optimal alignment.

14. The computer system of claim 13, wherein said polynucleotides having sequences (I) and (II) comprise Hyper-Variable Region 2 C-Stretch (HV2CS) mtDNA sequences.

15. The computer system of claim 14, wherein said initial alignment rule maximally preserves the HV2CS sequence AAACCCCCCCTCCCCC (SEQ ID NO:2) and also maximally preserves the TCCCCC region of the HV2CS sequence.

16. The method of claim 15, wherein said hierarchical set of alignment rules comprises
at least one additional hierarchically ordered alignment rule selected from the group consisting of:
(1) selecting the possible alignments with the lowest number of differences between sequence (I) and sequence (II);
(2) selecting those alignments containing transitions rather than transversions;
(3) selecting those alignments which place insertions or deletions 3' to any homopolymeric stretches present in said sequences (I) and (II);
(4) selecting those alignments in which insertions or deletions are placed contiguously; and
(5) selecting those alignments in which insertions or deletions are placed 3'-most.

17. The computer system of claim 13, wherein, in said step (A), said set of possible alignments contains a subset of the set of every possible alignment between said sequences (I) and (II).

18. The computer system of claim 13, wherein, in said step (A), said set of possible alignments contains every possible alignment between said sequences (I) and (II).

19. The computer system of claim 11, wherein said additional alignment rules comprise a rule which maximally preserves an AC motif of the polynucleotide sequence and locates any insertions or deletions 3' to the AC motif, wherein the AC motif is ACACACACACC (SEQ ID NO:1).

20. The computer system of claim 13,
wherein said initial alignment rule comprises selecting from said set of possible alignments the possible alignments with the lowest number of differences between sequence (I) and sequence (II) and eliminating all other alignments from said set of possible alignments; and
wherein said additional alignment rules comprise at least one rule selected from the group consisting of:
(1) a rule which maximally preserves an AC motif of the polynucleotide sequence and locates any insertions or deletions 3' to the AC motif, wherein the AC motif is ACACACACACC (SEQ ID NO:1);
(2) a rule preferring a transition substitution instead of a transversion;
(3) a rule in which insertions or deletions are placed contiguously;
(4) a rule that places insertions or deletions 3' to a homopolymeric stretch present in said sequences (I) and (II); and
(5) a rule in which insertions or deletions are placed 3'-most.

* * * * *

SEQUENCE LISTING

<160> NUMBER OF SEQ ID NOS: 41

<210> SEQ ID NO 1
<211> LENGTH: 11
<212> TYPE: DNA
<213> ORGANISM: Homo sapiens

<400> SEQUENCE: 1
acacacacac c                                                          11

<210> SEQ ID NO 2
<211> LENGTH: 16
<212> TYPE: DNA
<213> ORGANISM: Homo sapiens

<400> SEQUENCE: 2 aaacccccc tccccc                                                      16

<210> SEQ ID NO 3
<211> LENGTH: 18
<212> TYPE: DNA
<213> ORGANISM: Homo sapiens

<400> SEQUENCE: 3
aaaccctccc cccatgct                                                   18

```
<210> SEQ ID NO 4
<211> LENGTH: 19
<212> TYPE: DNA
<213> ORGANISM: Homo sapiens

<400> SEQUENCE: 4
aaaaccccct ccccatgct                                                    19

<210> SEQ ID NO 5
<211> LENGTH: 18
<212> TYPE: DNA
<213> ORGANISM: Homo sapiens

<400> SEQUENCE: 5
aaaacctccc cccatgct                                                     18

<210> SEQ ID NO 6
<211> LENGTH: 19
<212> TYPE: DNA
<213> ORGANISM: Homo sapiens

<400> SEQUENCE: 6
aaaaccccct ccccatgct                                                    19

<210> SEQ ID NO 7
<211> LENGTH: 18
<212> TYPE: DNA
<213> ORGANISM: Homo sapiens

<400> SEQUENCE: 7
aaaacctccc cccatgct                                                     18

<210> SEQ ID NO 8
<211> LENGTH: 19
<212> TYPE: DNA
<213> ORGANISM: Homo sapiens

<400> SEQUENCE: 8
aaaaccccct ccccatgct                                                    19

<210> SEQ ID NO 9
<211> LENGTH: 18
<212> TYPE: DNA
<213> ORGANISM: Homo sapiens

<400> SEQUENCE: 9
aaaacctccc cccatgct                                                     18

<210> SEQ ID NO 10
<211> LENGTH: 19
<212> TYPE: DNA
<213> ORGANISM: Homo sapiens

<400> SEQUENCE: 10
aaaaccccct ccccatgct                                                    19

<210> SEQ ID NO 11
<211> LENGTH: 16
<212> TYPE: DNA
<213> ORGANISM: Homo sapiens

<400> SEQUENCE: 11
agcacacaca caccgc                                                       16
```

```
<210> SEQ ID NO 12
<211> LENGTH: 14
<212> TYPE: DNA
<213> ORGANISM: Homo sapiens

<400> SEQUENCE: 12
agcacacaca ccgc                                                      14

<210> SEQ ID NO 13
<211> LENGTH: 16
<212> TYPE: DNA
<213> ORGANISM: Homo sapiens

<400> SEQUENCE: 13
agcacacaca caccgc                                                    16

<210> SEQ ID NO 14
<211> LENGTH: 14
<212> TYPE: DNA
<213> ORGANISM: Homo sapiens

<400> SEQUENCE: 14
agcacacaca ccgc                                                      14

<210> SEQ ID NO 15
<211> LENGTH: 16
<212> TYPE: DNA
<213> ORGANISM: Homo sapiens

<400> SEQUENCE: 15
tcaaaacccc ctcccc                                                    16

<210> SEQ ID NO 16
<211> LENGTH: 17
<212> TYPE: DNA
<213> ORGANISM: Homo sapiens

<400> SEQUENCE: 16
tcaaaccccc tccccccc                                                  17

<210> SEQ ID NO 17
<211> LENGTH: 16
<212> TYPE: DNA
<213> ORGANISM: Homo sapiens

<400> SEQUENCE: 17
tcaaaacccc ctcccc                                                    16

<210> SEQ ID NO 18
<211> LENGTH: 17
<212> TYPE: DNA
<213> ORGANISM: Homo sapiens

<400> SEQUENCE: 18
tcaaaccccc tccccccc                                                  17

<210> SEQ ID NO 19
<211> LENGTH: 21
<212> TYPE: DNA
<213> ORGANISM: Homo sapiens

<400> SEQUENCE: 19
tattttcgtc tgggggtat g                                               21
```

```
<210> SEQ ID NO 20
<211> LENGTH: 22
<212> TYPE: DNA
<213> ORGANISM: Homo sapiens

<400> SEQUENCE: 20
tacgtttcgt ctgggggtg tg                                              22

<210> SEQ ID NO 21
<211> LENGTH: 21
<212> TYPE: DNA
<213> ORGANISM: Homo sapiens

<400> SEQUENCE: 21
tattttcgtc tgggggtat g                                               21

<210> SEQ ID NO 22
<211> LENGTH: 22
<212> TYPE: DNA
<213> ORGANISM: Homo sapiens

<400> SEQUENCE: 22
tacgtttcgt ctgggggtg tg                                              22

<210> SEQ ID NO 23
<211> LENGTH: 10
<212> TYPE: DNA
<213> ORGANISM: Homo sapiens

<400> SEQUENCE: 23
attttcccct                                                           10

<210> SEQ ID NO 24
<211> LENGTH: 13
<212> TYPE: DNA
<213> ORGANISM: Homo sapiens

<400> SEQUENCE: 24
attttttccc cct                                                       13

<210> SEQ ID NO 25
<211> LENGTH: 10
<212> TYPE: DNA
<213> ORGANISM: Homo sapiens

<400> SEQUENCE: 25
attttcccct                                                           10

<210> SEQ ID NO 26
<211> LENGTH: 13
<212> TYPE: DNA
<213> ORGANISM: Homo sapiens

<400> SEQUENCE: 26
attttttccc cct                                                       13

<210> SEQ ID NO 27
<211> LENGTH: 14
<212> TYPE: DNA
<213> ORGANISM: Homo sapiens

<400> SEQUENCE: 27
aatccacatc aaaa                                                      14
```

```
<210> SEQ ID NO 28
<211> LENGTH: 13
<212> TYPE: DNA
<213> ORGANISM: Homo sapiens

<400> SEQUENCE: 28
aacccacatc aaa                                                          13

<210> SEQ ID NO 29
<211> LENGTH: 14
<212> TYPE: DNA
<213> ORGANISM: Homo sapiens

<400> SEQUENCE: 29
aatccacatc aaaa                                                         14

<210> SEQ ID NO 30
<211> LENGTH: 13
<212> TYPE: DNA
<213> ORGANISM: Homo sapiens

<400> SEQUENCE: 30
aacccacatc aaa                                                          13

<210> SEQ ID NO 31
<211> LENGTH: 14
<212> TYPE: DNA
<213> ORGANISM: Homo sapiens

<400> SEQUENCE: 31
aaaaccccct cccc                                                         14

<210> SEQ ID NO 32
<211> LENGTH: 15
<212> TYPE: DNA
<213> ORGANISM: Homo sapiens

<400> SEQUENCE: 32
aaaccccccc ccccc                                                        15

<210> SEQ ID NO 33
<211> LENGTH: 14
<212> TYPE: DNA
<213> ORGANISM: Homo sapiens

<400> SEQUENCE: 33
aaaaccccct cccc                                                         14

<210> SEQ ID NO 34
<211> LENGTH: 15
<212> TYPE: DNA
<213> ORGANISM: Homo sapiens

<400> SEQUENCE: 34
aaaccccccc ccccc                                                        15

<210> SEQ ID NO 35
<211> LENGTH: 15
<212> TYPE: DNA
<213> ORGANISM: Homo sapiens

<400> SEQUENCE: 35
aaaaccccct cccca                                                        15
```

```
-continued

<210> SEQ ID NO 36
<211> LENGTH: 14
<212> TYPE: DNA
<213> ORGANISM: Homo sapiens

<400> SEQUENCE: 36
aaaaccccac ccca                                                        14

<210> SEQ ID NO 37
<211> LENGTH: 15
<212> TYPE: DNA
<213> ORGANISM: Homo sapiens

<400> SEQUENCE: 37 aaaacccct cccca                                                        15

<210> SEQ ID NO 38
<211> LENGTH: 14
<212> TYPE: DNA
<213> ORGANISM: Homo sapiens

<400> SEQUENCE: 38 aaaacccac ccca                                                         14

<210> SEQ ID NO 39
<211> LENGTH: 23
<212> TYPE: DNA
<213> ORGANISM: Homo sapiens

<400> SEQUENCE: 39
ccaccaaacc cccctcccc cgc                                               23

<210> SEQ ID NO 40
<211> LENGTH: 24
<212> TYPE: DNA
<213> ORGANISM: Homo sapiens

<400> SEQUENCE: 40
ccacaaaccc cccctcccc ccgc                                              24

<210> SEQ ID NO 41
<211> LENGTH: 17
<212> TYPE: DNA
<213> ORGANISM: Homo sapiens

<400> SEQUENCE: 41
ctggagccgg agcaccc                                                     17
```